(12) United States Patent
Eastham et al.

(10) Patent No.: US 7,485,739 B2
(45) Date of Patent: Feb. 3, 2009

(54) CATALYST SYSTEM

(75) Inventors: Graham Eastham, Wilton (GB); Ian Butler, Gwynedd (GB); Kevin Fortune, Bangkok (TH)

(73) Assignee: Lucite International UK Ltd., Wilton, Redcar (GB)

( * ) Notice: Subject to any disclaimer, the term of this patent is extended or adjusted under 35 U.S.C. 154(b) by 597 days.

(21) Appl. No.: 10/527,910

(22) PCT Filed: Sep. 10, 2003

(86) PCT No.: PCT/GB03/03936

§ 371 (c)(1),
(2), (4) Date: Aug. 24, 2005

(87) PCT Pub. No.: WO2004/024322

PCT Pub. Date: Mar. 25, 2004

(65) Prior Publication Data

US 2006/0252935 A1    Nov. 9, 2006

(30) Foreign Application Priority Data

| Sep. 12, 2002 | (GB) | 0221093.8 |
| Nov. 30, 2002 | (GB) | 0228018.8 |
| Apr. 30, 2003 | (GB) | 0309812.6 |
| Jul. 10, 2003 | (GB) | 0316159.3 |
| Aug. 6, 2003 | (WO) | PCT/GB03/003419 |

(51) Int. Cl.
*C07F 17/00* (2006.01)
*C07F 15/00* (2006.01)
*B01J 31/00* (2006.01)

(52) U.S. Cl. .............. 556/22; 556/136; 556/141; 568/387; 546/2; 502/152; 502/153

(58) Field of Classification Search ............ 556/22, 556/136, 141; 546/2; 568/387; 502/152, 502/153
See application file for complete search history.

(56) References Cited

U.S. PATENT DOCUMENTS

| 5,563,308 A | 10/1996 | Spindler et al. |
| 5,760,264 A | 6/1998 | Brieden |
| 5,783,715 A | 7/1998 | Pugin |
| 6,015,919 A | 1/2000 | Pugin |
| 6,169,192 B1 | 1/2001 | Pugin |
| 6,191,284 B1 | 2/2001 | Knochel et al. |
| 6,258,979 B1 | 7/2001 | Kagan et al. |
| 6,284,925 B1 | 9/2001 | Knochel et al. |
| 6,337,406 B1 | 1/2002 | Zhang |
| 6,521,769 B1 | 2/2003 | Zhang |

FOREIGN PATENT DOCUMENTS

| EP | 0 662 467 | 7/1995 |
| WO | WO 96/19434 | 6/1996 |

OTHER PUBLICATIONS

International Search Report issued Mar. 2, 2004 in PCT/GB03/03936.
Hendrikus C.L. Abbenhuis et al., "Successful Application of a Forgotten Phosphine in Asymmetric Catalysis: A 0-Phisphabicyclo[3.3.1]non-9-yl Ferrocene Derivative as Chiral Ligand", Oragnometallics, vol. 14, 1995, pp. 759-766.
William C. Cullen et al., "Structure of the Hydrogenation Catalyst [(PP)Rh(NBC)]CI04, PP=$n^5$—[$(CH_3)_3C]_2PC_5H_4)_2$Fe, and Some Comparative Rate Studies", Organometallics, vol. 2, 1983, pp. 714-719.

*Primary Examiner*—Porfirio Nazario Gonzalez
(74) *Attorney, Agent, or Firm*—Jones Day

(57) ABSTRACT

A catalyst suitable for carbonylating ethylenically unsaturated compounds comprising a Group VIIIB metal or compound thereof and a metallocene.

52 Claims, No Drawings

CATALYST SYSTEM

CROSS REFERENCE TO RELATED APPLICATIONS

This application is the National Phase application of International Application No. PCT/GB03/003936 filed Sep. 10, 2003, which designated the United States and was published in English. The International application further claims priority to International Application No. PCT/GB031003419, filed Aug. 6, 2003, which was published in English. The International applications, in their entirety, are incorporated herein by reference.

The present invention relates to compounds, in particular compounds for catalysing the carbonylation of ethylenically unsaturated compounds, methods of preparing such compounds and the use of such compounds for catalysing the carbonylation of ethylenically unsaturated compounds.

The carbonylation of ethylenically unsaturated compounds using carbon monoxide in the presence of a catalyst system and an alcohol or water to yield the corresponding ester or carboxylic acid, respectively, is well known. Suitable catalyst systems comprise a Group VIII metal (e.g. palladium) and a phosphine ligand (e.g. an alkyl phosphine or a bidentate phosphine ligand as disclosed in WO-A-9619434).

Although catalyst systems have been developed which exhibit reasonable stability during the carbonylation process and permit relatively high reaction rates to be achieved, there still exists a need for improved catalyst systems. Suitably, the present invention aims to provide an improved catalyst for carbonylating ethylenically unsaturated compounds.

According to a first aspect, the present invention provides a catalyst suitable for carbonylating an ethylenically unsaturated compound, which catalyst is obtainable by combining:

(a) a Group VIIIB metal or a compound thereof; and,
(b) a compound of formula I or salt thereof:

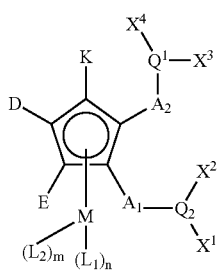

(I)

wherein:

$A_1$ and $A_2$, and $A_3$, $A_4$ and $A_5$ (when present), each independently represent lower alkylene;

K is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_3$-$Q^3$($X^5$)$X^6$;

D is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_4$-$Q^4$($X^7$)$X^8$;

E is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_5$-$Q^5$($X^9$)$X^{10}$;

or both D and E together with the carbon atoms of the cyclopentadienyl ring to which they are attached form an optionally substituted phenyl ring;

$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-tricyclo [3.3.1.1{3,7}]decyl group or derivative thereof, or $X^1$ and $X^2$ together with $Q^2$ to which they are attached form a ring system of formula 1a

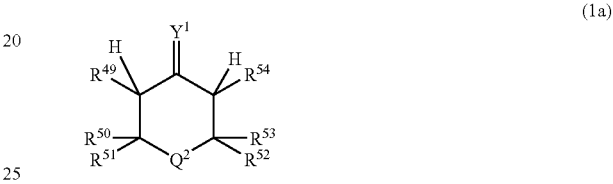

(1a)

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula 1b

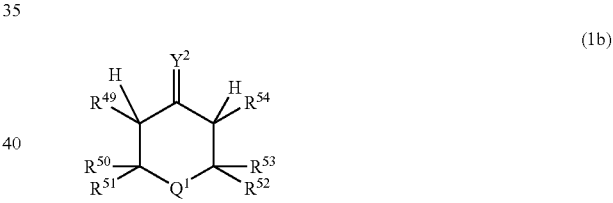

(1b)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula 1c

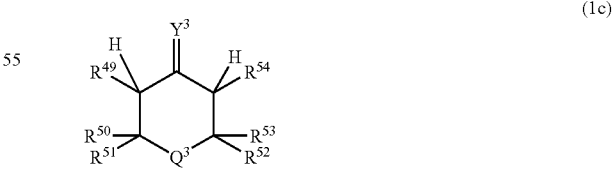

(1c)

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1{3,7}]decyl group or derivative thereof, or $X^7$ and $X^8$ together with $Q^4$ to which they are attached form a ring system of formula 1d

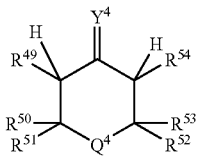

(1d)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7)}] decyl group or derivative thereof, or $X^9$ and $X^{10}$ together with $Q^5$ to which they are attached form a ring system of formula 1e

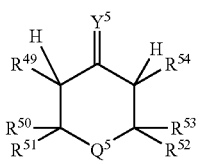

(1e)

$Q^1$ and $Q^2$, and $Q^3$, $Q^4$ and $Q^5$ (when present), each independently represent phosphorus, arsenic or antimony;

M represents a Group VIB or VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or $N-R^{55}$;

n=0 or 1;

and m=0 to 5;

provided that when n=1 then m equals 0, and when n equals 0 then m does not equal 0.

Such compounds are referred to hereinafter as "the compounds of the invention".

Preferably in a compound of formula I when both K represents $-A_3-Q^3(X^5)X^6$ and E represents $-A_5-Q^5(X^9)X^{10}$, then D represents $-A_4-Q^4(X^7)X^8$.

Suitably, the compounds of the invention may catalyse the carbonylation of unsaturated compounds, particularly ethylenically unsaturated compounds, in the presence of carbon monoxide and a coreactant. In particular, the compounds of the invention may be employed in hydroformylation reactions, hydrocarboxylation reactions, hydroesterification reactions and hydroamidation reactions. For example, the compounds of the invention may catalyse the conversion of an ethylenically unsaturated compound in the presence of carbon monoxide and a hydroxyl group containing compound to the corresponding carboxylic acid or ester, respectively, depending on the choice of hydroxyl group containing compound used (i.e. a carboxylic acid if the hydroxyl group containing compound is water and an ester if the hydroxyl group containing compound is an alcohol.

Conveniently, the compounds of the invention may exhibit a high stability under typical carbonylation reaction conditions such that they require little or no replenishment. Conveniently, the compounds of the invention may increase the rate of the carbonylation reaction of an ethylenically unsaturated compound compared to known catalysts. Conveniently, the compounds of the invention may promote high conversion rates of the ethylenically unsaturated compound, thereby yielding the desired product in high yield with little or no impurities. Consequently, employing the compounds of the invention may increase the commercial viability of a carbonylation process, such as the carbonylation of an ethylenically unsaturated compound. Suitably, the compounds of the invention typically exhibit a high catalytic turnover in the carbonylation of an unsaturated compound, particularly an ethylenically unsaturated compound, in the presence of carbon monoxide and a co-reactant as defined herein.

Unexpectedly, it has been found that if the carbon atoms of $X^1$ and $X^2$ bonded to $Q^2$ and the carbon atoms of $X^3$ and $X^4$ bonded to $Q^1$ in the compound of formula I do not include a hydrogen atom, then this typically produces a catalyst which exhibits increased catalytic turnover in the carbonylation of an unsaturated compound compared with a comparable compound where a carbon atom present in $X^1$ and/or $X^2$, and $X^3$ and/or $X^4$ bonded to $Q^2$ and $Q^1$, respectively, includes a hydrogen atom. Most preferably, $Q^1$ is bonded to a tertiary carbon atom of both $X^3$ and $X^4$, and $Q^2$ is bonded to a tertiary carbon atom of both $X^1$ and $X^2$. Similarly, if present, the carbon atoms of $X^5$ and $X^6$, bonded to $Q^3$, of $X^7$ and $X^8$ bonded to $Q^4$, and of $X^9$ and $X^{10}$ bonded to $Q^5$ do not include a hydrogen atom. More preferably, $Q^3$, $Q^4$ and $Q^5$, if present, are bonded to a tertiary carbon atom of both $X^5$ and $X^6$, $X^7$ and $X^8$, and $X^9$ and $X^{10}$, respectively.

Preferably, $R^1$ to $R^{18}$ and $R^{31}$ to $R^{42}$, when present, each independently represent hydrogen, optionally substituted $C_1$ to $C_6$ alkyl, $C_1$-$C_6$ alkyl phenyl (wherein the phenyl group is optionally substituted as defined herein), trifluoromethyl or phenyl (wherein the phenyl group is optionally substituted as defined herein). Even more preferably, $R^1$ to $R^{18}$ and $R^{31}$ to $R^{42}$, when present, each independently represent hydrogen, $C_1$ to $C_6$ alkyl, which is optionally substituted as defined herein, trifluoromethyl or optionally substituted phenyl. Even more preferably, $R^1$ to $R^{18}$ and $R^{31}$ to $R^{42}$, when present each independently represent hydrogen, non-substituted $C_1$ to $C_6$ alkyl or phenyl which is optionally substituted with one or more substituents selected from non-substituted $C_1$ to $C_6$ alkyl or $OR^{19}$ where $R^{19}$ represents hydrogen or unsubstituted $C_1$ to $C_6$ alkyl. More preferably, $R^1$ to $R^{18}$ and $R^{31}$ to $R^{42}$, when present, each independently represent hydrogen or non-substituted $C_1$ to $C_6$ alkyl such as methyl, ethyl, n-propyl, iso-propyl, n-butyl, iso-butyl, tert-butyl, pentyl, hexyl and cyclohexyl, especially methyl. Most preferably, $R^1$ to $R^{18}$ and $R^{31}$ to $R^{42}$ when present, each independently represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

Alternatively, or additionally, one or more of the groups $R^1$ to $R^3$, $R^4$ to $R^6$, $R^7$ to $R^9$, $R^{10}$ to $R^{12}$, $R^{13}$ to $R^{15}$, $R^{16}$ to $R^{18}$, $R^{31}$ to $R^{33}$, $R^{34}$ to $R^{36}$, $R^{37}$ to $R^{39}$ or $R^{40}$ to $R^{42}$ (when present) together with the carbon atom to which they are attached independently may form cyclic alkyl structures such as 1-norbornyl or 1-norbornadienyl.

Alternatively, or additionally, one or more of the groups $R^1$ and $R^2$, $R^4$ and $R^5$, $R^7$ and $R^8$, $R^{10}$ and $R^{11}$, $R^{13}$ and $R^{14}$, $R^{16}$ and $R^{17}$, $R^{31}$ and $R^{32}$, $R^{34}$ and $R^{35}$, $R^{37}$ and $R^{38}$ or $R^{40}$ and $R^{41}$ (when present) together with the carbon atom to which they are attached independently may form a cyclic alkyl structures, preferably a $C_5$ to $C_7$ cyclic alkyl structure such as cyclohexyl and cyclopentyl, and $R^3$, $R^6$, $R^9$, $R^{12}$, $R^{15}$, $R^{18}$, $R^{33}$, $R^{36}$, $R^{39}$ and $R^{42}$ (when present) each independently represent hydrogen, lower alkyl, trifluoromethyl or aryl as defined above, particularly non-substituted $C_{1\ to\ C6}$ alkyl and hydrogen, especially non-substituted $C_1$ to $C_6$ alkyl.

In an especially preferred embodiment, each of $R^1$ to $R^{18}$ and $R^{31}$ to $R^{42}$, when present, do not represent hydrogen. Suitably, such an arrangement means $Q^1$, $Q^2$, $Q^3$, $Q^4$ and $Q^5$ are bonded to a carbon atom of $X^1$ to $X^{10}$, respectively, which bears no hydrogen atoms.

Preferably, $R^1$, $R^4$, $R^7$, $R^{10}$, $R^{13}$, $R^{16}$, $R^{31}$, $R^{34}$, $R^{37}$ and $R^{40}$ (when present), each represent the same substituent as defined herein; $R^2$, $R^5$, $R^8$, $R^{11}$, $R^{14}$, $R^{17}$, $R^{32}$, $R^{35}$, $R^{38}$ and $R^{41}$ (when present), each represent the same substituent as defined herein; and $R^3$, $R^6$, $R^9$, $R^{12}$, $R^{15}$, $R^{18}$, $R^{33}$, $R^{36}$, $R^{39}$ and $R^{42}$ (when present), each represent the same substituent as defined herein. More preferably $R^1$, $R^4$, $R^7$, $R^{10}$, $R^{13}$, $R^{16}$, $R^{31}$, $R^{34}$, $R^{37}$ and $R^{40}$ (when present) each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl, or trifluoromethyl; $R^2$, $R^5$, $R^8$, $R^{11}$, $R^{14}$, $R^{17}$, $R^{32}$, $R^{35}$, $R^{38}$ and $R^{41}$ (when present), each independently represent the same $C_1$-$C_6$ alkyl as defined above, or trifluoromethyl; and $R^3$, $R^6$, $R^9$, $R^{12}$, $R^{15}$, $R^{18}$, $R^{33}$, $R^{36}$, $R^{39}$ and $R^{42}$ (when present), each independently represent the same $C_1$-$C_6$ alkyl as defined above, or trifluoromethyl. For example: $R^1$, $R^4$, $R^7$, $R^{10}$ $R^{13}$ and $R^{16}$ (when present) each represent methyl; $R^2$, $R^5$, $R^8$, $R^{11}$, $R^{14}$ and $R^{17}$ each represent ethyl (when present); and, $R^3$, $R^6$, $R^9$, $R^{12}$, $R^{15}$ and $R^{18}$ (when present) each represent n-butyl or n-pentyl.

In an especially preferred embodiment of the present invention each $R^1$ to $R^{18}$ and $R^{31}$ to $R^{42}$ group (when present) represents the same substituent as defined herein. Preferably, each $R^1$ to $R^{18}$ and $R^{31}$ to $R^{42}$ group represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl, or trifluoromethyl. Most preferably, each $R^1$ to $R^{18}$ and $R^{31}$ to $R^{42}$ group represents non-substituted $C_1$-$C_6$ alkyl, particularly methyl.

The term adamantyl when used herein means an adamantyl group which may be bonded to $Q^1$, $Q^2$, $Q^3$, $Q^4$ and $Q^5$, respectively, in position 1 or 2. Tricyclo[3.3.1.1.{3,7}]decyl is the systematic name for an adamantyl group, suitably $Q^1$, $Q^2$, $Q^3$, $Q^4$ and $Q^5$, respectively, may be bonded to the 1 position or 2 position of one or two tricyclo[3.3.1.1.{3,7}] decyl groups. Preferably, $Q^1$ and $Q^2$, and $Q^3$, $Q^4$ and $Q^5$, when present, is bonded to a tertiary carbon of one or more adamantyl groups. Suitably, when the adamantyl group represents unsubstituted adamantyl, $Q^1$ and $Q^2$, and $Q^3$, $Q^4$ and $Q^5$ when present are preferably bonded to the 1 position of one or more tricyclo[3.3.1.1{3,7}]decyl groups i.e. the carbon atom of the adamantyl group bears no hydrogen atom.

The adamantyl group may optionally comprise, besides hydrogen atoms, one or more substituents selected from lower alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)(R^{27})R^{28}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$ lower alkyl, cyano and aryl are as defined herein and $R^{56}$ to $R^{62}$ each independently represent hydrogen, lower alkyl, aryl or Het.

Suitably, when the adamantyl group is substituted with one or more substituents as defined above, highly preferred substituents include unsubstituted $C_{1\ to\ C8}$ alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, —$C(O)N(R^{25})R^{26}$ and —$PO(R^{58})(R^{59})$, —$CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{53}$, $R^{56}$ each independently represent unsubstituted $C_1$-$C_8$ alkyl or phenyl.

Suitably, the adamantyl group may comprises, besides hydrogen atoms, up to 10 substituents as defined above, preferably up to 5 substituents as defined above, more preferably up to 3 substituents as defined above. Suitably, when the adamantyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl group comprises hydrogen atoms only i.e. the adamantyl group is not substituted.

Preferably, when more than one adamantyl group is present in a compound of formula I, each adamantyl group is identical.

By the term 2-phospha-tricyclo[3.3.1.1.{3,7}]decyl group we mean a 2-phospha-adamantyl group formed by the combination of $X^1$ and $X^2$ together with $Q^2$ to which they are attached, a 2-phospha-adamantyl group formed by the combination of $X^3$ and $X^4$ together with $Q^1$ to which they are attached, a 2-phospha-adamantyl group formed by the combination of $X^5$ and $X^6$ together with $Q^3$ to which they are attached, a 2-phospha-adamantyl group formed by the combination of $X^7$ and $X^8$ together with $Q^4$ to which they are attached and a 2-phospha-adamantyl group formed by the combination of $X^9$ and $X^{10}$ together with $Q^5$ to which they are attached, wherein $Q^1$, $Q^2$, $Q^3$, $Q^4$ and $Q^5$ is in the 2-position of the adamantyl group of which it forms an integral part and each of $Q^1$, $Q^2$, $Q^3$, $Q^4$ and $Q^5$ represents phosphorus.

The 2-phospha-tricyclo[3.3.1.1.{3,7}]decyl group (referred to as 2-phospha-adamantyl group herein) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-phospha-adamantyl group includes more than one substituent, preferably each substituent is identical.

Preferably, the 2-phospha-adamantyl group is substituted on one or more of the 1, 3, 5 or 7 positions with a substituent as defined herein. More preferably, the 2-phospha-adamantyl group is substituted on each of the 1, 3 and 5 positions. Suitably, such an arrangement means the phosphorous atom of the 2-phospha-adamantyl group is bonded to carbon atoms in the adamantyl skeleton having no hydrogen atoms. Most preferably, the 2-phospha-adamantyl group is substituted on each of the 1, 3, 5 and 7 positions. When the 2-phospha-adamantyl group includes more than 1 substituent preferably each substituent is identical. Especially preferred substituents are unsubstituted $C_1$-$C_8$ alkyl and trifluoromethyl, particularly unsubstituted $C_1$-$C_8$ alkyl such as methyl.

Preferably, the 2-phospha-adamantyl group includes additional heteroatoms, other than the 2-phosphorous atom, in the 2-phospha-adamantyl skeleton. Suitable additional heteroatoms include oxygen and sulphur atoms, especially oxygen atoms. More preferably, the 2-phospha-adamantyl group includes one or more additional heteroatoms in the 6, 9 and 10 positions. Even more preferably, the 2-phospha-adamantyl group includes an additional heteroatom in each of the 6, 9 and 10 positions. Most preferably, when the 2-phospha-adamantyl group includes two or more additional heteroatoms in the 2-phospha-adamantyl skeleton, each of the additional heteroatoms are identical. An especially preferred 2-phospha-adamantyl group, which may optionally be substituted with one or more substituents as defined herein, includes an oxygen atom in each of the 6, 9 and 10 positions of the 2-phospha-adamantyl skeleton.

Highly preferred 2-phospha-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospa-1,3,5,-trimethyl-6,9,10-trioxadamantyl group.

Preferably, when more than one 2-phospha-adamantyl group is present in a compound of formula I, each 2-phospha-adamantyl group is identical.

The term congressyl when used herein means a congressyl group (also known as diamantyl group) which may be bonded to $Q^1$, $Q^2$, $Q^3$, $Q^4$ and $Q^5$ respectively. Preferably, $Q^1$ and $Q^2$, and $Q^3$, $Q^4$ and $Q^5$, when present, is bonded to one of the tertiary carbon atoms of the congressyl groups. Suitably, when the congressyl group is unsubstituted, $Q^1$ and $Q^2$, and $Q^3$, $Q^4$ and $Q^5$ when present, are preferably bonded to the 1-position of one or more congressyl groups.

The congressyl group may optionally comprise, beside hydrogen atoms, one or more substituents. Suitable substituents include those substituents as defined herein in respect of the adamantyl group. Highly preferred substituents include unsubstituted $C_1$-$C_6$ alkyl groups, particularly methyl, and trifluoromethyl. Most preferably, the congressyl group is unsubstituted and comprises hydrogen atoms only.

Preferably, when more than one congressyl group is present in a compound of formula I, each congressyl group is identical.

Preferably, where one or more ring systems of formula Ia, Ib, Ic, Id or Ie are present in a compound of formula I, $R^{50}$ to $R^{53}$ each independently represent lower alkyl, aryl or Het, which groups are optionally substituted and/or terminated as defined herein. Such an arrangement means $Q^2$, $Q^1$, $Q^3$, $Q^4$ and $Q^5$ of the ring system of formula Ia to Ie, respectively, is not bonded to a carbon atom bearing a hydrogen atom. Even more preferably, $R^{50}$ to $R^{53}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, or trifluoromethyl. Even more preferably $R^{50}$ to $R^{53}$ each represent the same group as defined herein, particularly non-substituted $C_1$-$C_6$ alkyl, especially methyl.

Preferably, where one or more ring system of formula Ia to Ie are present in a compound of formula I, $R^{49}$ and $R^{54}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, trifluoromethyl or hydrogen. More preferably, $R^{49}$ and $R^{54}$ represent the same group as defined herein, especially hydrogen.

Preferably, where one or more ring systems of formula Ia to Ie are present in a compound of formula I, $Y^1$ to $Y^5$ are identical. Most preferably, each of $Y^1$ to $Y^5$ represents oxygen. Preferably, where more than one ring system of formula Ia to Ie is present in a compound of formula I, each such ring system is identical.

Preferred embodiments of the present invention include those wherein:

$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;

$X^1$ represents $CR^1(R^2)(R^3)$, $X^2$ represents congressyl, $X^3$ represents $CR^7(R^8)(R^9)$ and $X^4$ represents congressyl;

$X^1$ represents $CR^1(R^2)(R^3)$, $X^2$ represents $CR^4(R^5)(R^6)$, and $X^3$ and $X^4$ together with $Q^1$ to which they are attached form a ring system of formula Ib or a 2-phospha-adamantyl group;

$X^1$ represents $CR^1(R^2)(R^3)$, $X^2$ represents adamantyl, $X^3$ and $X^4$ together with $Q^1$ to which they are attached form a ring system of formula Ib or a 2-phospha-adamantyl group;

$X^1$ represents $CR^1(R^2)(R^3)X^2$ represents congressyl, $X^3$ and $X^4$ together with $Q^1$ to which they are attached form a ring system of formula Ib or a 2-phospha-adamantyl group;

$X^1$ to $X^4$ each independently represent adamantyl;

$X^1$ to $X^4$ each independently represent congressyl;

$X^1$ and $X^2$ each independently represent adamantyl and $X^3$ and $X^4$ each independently represent congressyl;

$X^1$ and $X^3$ independently represent adamantyl and $X^2$ and $X^4$ independently represent congressyl;

$X^1$ and $X^2$ independently represent adamantyl, $X^3$ represents $CR^7(R^8)(R^9)$ and $X^4$ represents $CR^{10}(R^{11})(R^{12})$;

$X^1$ and $X^2$ independently represent congressyl, $X^3$ represents $CR^7(R^8)(R^9)$ and $X^4$ represents $CR^{10}(R^{11})(R^{12})$;

$X^1$ and $X^2$ independently represent adamantyl, and $X^3$ and $X^4$ together with $Q^1$ to which they are attached form a ring system of formula Ib or a 2-phospha-adamantyl group;

$X^1$ and $X^2$ independently represent congressyl, and $X^3$ and $X^4$ together with $Q^1$ to which they are attached form a ring system of formula Ib or a 2-phospha-adamantyl group;

$X^1$ and $X^2$ together with $Q^2$ to which they are attached form a ring system of formula Ia, and $X^3$ and $X^4$ together with $Q^1$ to which they are attached form a ring system of formula Ib;

$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Highly preferred embodiments of the present invention include those wherein:

$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;

$X^1$ represents $CR^1(R^2)(R^3)$, $X^2$ represents congressyl, $X^3$ represents $CR^7(R^8)(R^9)$ and $X^4$ represents congressyl;

$X^1$ to $X^4$ each independently represent adamantyl;

$X^1$ to $X^4$ each independently represent congressyl;

$X^1$ and $X^2$ together with $Q^2$ to which they are attached form a ring system of formula Ia, and $X^3$ and $X^4$ together with $Q^1$ to which they are attached form a ring system of formula Ib;

$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Preferably in a compound of formula I, $X^1$ is identical to $X^3$ and $X^2$ is identical to $X^4$. More preferably, $X^1$ is identical to $X^3$ and $X^5$, $X^7$ and $X^9$ when present, and $X^2$ is identical to $X^4$ and $X^6$, $X^8$ and $X^{10}$ when present. Even more preferably, $X^1$ to $X^4$ are identical. Most preferably, $X^1$ to $X^4$ are identical to each of $X^6$ to $X^{10}$ when present.

Preferably, in the compound of formula I, $X^1$ and $X^2$ represent identical substituents, $X^3$ and $X^4$ represent identical substituents, $X^5$ and $X^6$ (when present) represent identical substituents, $X^7$ and $X^8$ (when present) represent identical substituents, and $X^9$ and $X^{10}$ (when present) represent identical substituents.

Preferably, in a compound of formula I, K represents -$A_3$-$Q^3(X^5)X^6$, hydrogen, lower alkyl, —$CF_3$, phenyl or lower alkyl phenyl. More preferably, K represents -$A_3$-$Q^3(X^5)X^6$, hydrogen, unsubstituted $C_1$-$C_6$ alkyl, unsubstituted phenyl, trifluoromethyl or $C_1$-$C_6$ alkyl phenyl.

In a particular preferred embodiment K in a compound of formula I represents hydrogen.

In an alternative embodiment where K does not represent hydrogen, K represents -$A_3$-$Q^3(X^5)X^6$. Preferably, $X^5$ is identical to $X^3$ or $X^1$, and $X^6$ is identical to $X^2$ or $X^4$. More preferably, $X^5$ is identical to both $X^3$ and $X^1$, and $X^6$ is identical to both $X^2$ and $X^4$. Even more preferably, -$A_3$-$Q^3(X^5)X^6$ is identical to either -$A_1$-$Q^2(X^1)X^2$ or -$A_2$-$Q^1(X^3)X^4$. Most preferably, -$A_3$-$Q^3(X^5)X^6$ is identical to both -$A_1$-$Q^2(X^1)X^2$ and -$A_2$-$Q^1(X^3)X^4$.

Most preferably, K represents hydrogen in a compound of formula I.

Preferably, in the compound of formula I, D represents -$A_4$-$Q^4(X^7)X^8$, hydrogen, lower alkyl, $CF_3$, phenyl or lower alkylphenyl, and E represents -$A_5$-$Q^5(X^9)X^{10}$, hydrogen, lower alkyl, $CF_3$, phenyl or lower alkylphenyl, or D and E together with the carbons of the cyclopentadienyl ring to which they are attached form an optionally substituted phenyl ring. More preferably, D represents -$A_4$-$Q^4(X^7)X^8$, hydrogen, phenyl, $C_1$-$C_6$ alkylphenyl, unsubstituted $C_1$-$C_6$ alkyl, such as methyl, ethyl, propyl, butyl, pentyl and hexyl, or $CF_3$; E represents -$A_5$-$Q^5(X^9)X^{10}$, hydrogen, phenyl, $C_1$-$C_6$ alkylphenyl, unsubstituted $C_1$-$C_6$ alkyl such as methyl, ethyl, propyl, butyl, pentyl and hexyl, or —$CF_3$; or both D and E together with the carbon atoms of the cyclopentadienyl ring to which they are attached form a phenyl ring which is optionally substituted with one or more groups selected from phenyl, $C_1$-$C_6$ alkylphenyl, unsubstituted $C_1$-$C_6$ alkyl or —$CF_3$.

Suitably, when D and E together with the carbon atoms of the cyclopentadienyl ring to which they are attached form an optionally substituted phenyl ring, the metal M or cation thereof is attached to an indenyl ring system.

In a particular preferred embodiment, D in a compound of formula I, represents hydrogen.

In an alternative embodiment where D does not represent hydrogen, D represents -$A$-$Q^4(X^7)X^8$. Preferably $X^8$ is identical to $X^4$ or $X^2$, and $X^7$ is identical to $X^1$ or $X^3$. More preferably, $X^8$ is identical to both $X^4$ and $X^2$, and $X^7$ is identical to both $X^1$ and $X^3$. Even more preferably, -$A_4$-$Q^4(X^7)X^8$ is identical to either -$A_1$-Q $(X^1)X^2$ or -$A_2$-$Q^1(X^3)X^4$.

Most preferably, -$A_4$-$Q^4(X^7)X^8$ is identical to both -$A_2$-$Q^1(X^3)X^4$, and -$A_3$-$Q^3(X^5)X^6$ if present.

In a particular preferred embodiment, E in a compound of formula I represents hydrogen.

In an alternative embodiment where E does not represent hydrogen, E represents -$A_5$-$Q^5(X^9)X^{10}$. Preferably $X^{10}$ is identical to $X^4$ or $X^2$, and $X^9$ is identical to $X^1$ or $X^3$. More preferably, $X^{10}$ is identical to both $X^4$ and $X^2$, and $X^9$ is identical to $X^1$ and $X^3$. Even more preferably, -$A_5$-$Q^5(X^9)X^{10}$ is identical to either -$A_1$-$Q^2(X^1)X^2$ or -$A_2$-$Q^1(X^3)X^4$. Most preferably, -$A_5$-$Q^5(X^9)X^{10}$ is identical to both -$A_1$-$Q^2(X^1)X^2$ and $A_2$-$Q^1(X^3)X^4$, and -$A_3$-$Q^3(X^5)X^6$ and -$A_4$-$Q^4(X^7)X^8$ if present.

Preferably, in the compound of formula I, when D and E together with the carbon atoms of the cyclopentadienyl ring to which they are attached do not form an optionally substituted phenyl ring, each of K, D and E represent an identical substituent.

In an alternative preferred embodiment, D and E together with the carbons of the cyclopentadienyl ring to which they are attached form an unsubstituted phenyl ring.

Highly preferred embodiments of compounds of formula I include those wherein:

K, D and E are identical substituents as defined herein, particularly where K, D and E represent hydrogen;

K represents hydrogen, and D and E together with the carbons of the cyclopentadienyl ring to which they are attached form an unsubstituted phenyl ring;

K represents -$A_3$-$Q^3(X^5)X^6$ as defined herein and both D and E represent H;

K represents -$A_3$-$Q^3(X^5)X^6$ as defined herein and D and E together with the carbon atoms of the cyclopentadienyl ring to which they are attached form an unsubstituted phenyl ring;

K represents -$A_3$-$Q^3(X^5)X^6$, D represents -$A_4$-$Q^4(X^7)X^8$ and E represents -$A_5$-$Q^5(X^9)X^{10}$.

Especially preferred compounds of formula I include those where both D and E represent hydrogen or D and E together with the carbon atoms of the cyclopentadienyl ring to which they are attached form an unsubstituted phenyl ring, particularly those compounds where both D and E represent hydrogen.

Preferably, in the compound of formula I, $A_1$ and $A_2$, and $A_3$, $A_4$ and $A_5$ (when present), each independently represent $C_1$ to $C_6$ alkylene which is optionally substituted as defined herein, for example with lower alkyl groups. Suitably, $A_1$ and $A_2$, and $A_3$, $A_4$ and $A_5$ (when present) may include a chiral carbon atom. Preferably, the lower alkylene groups which $A_1$ to $A_5$ may represent are non-substituted. A particular preferred lower alkylene, which $A_1$ to $A_5$ may independently represent, is —$CH_2$— or —$C_2H_4$—. Most preferably, each of $A_1$ and $A_2$, and $A_3$, $A_4$ and $A_5$ (when present), represent the same lower alkylene as defined herein, particularly —$CH_2$—.

In the compound of formula I, preferably each $Q^1$ and $Q^2$, and $Q^3$, $Q^4$ and $Q^5$ (when present) are the same. Most preferably, each $Q^1$ and $Q^2$, and $Q^3$, $Q^4$ and $Q^5$ (when present), represents phosphorus.

It will be appreciated by those skilled in the art that the compounds of formula I (referred to as (b) above) may function as ligands that coordinate with the Group VIIIB metal or compound thereof (referred to as (a) above) to form the compounds of the invention. Typically, the Group VIIIB metal or compound thereof (a) coordinates to the one or more phosphorus, arsenic and/or antimony atoms of the compound of formula I. It will be appreciated that the compounds of formula I may be referred to broadly as "metallocenes".

Suitably, when n=1 and $L_1$ represents an optionally substituted cyclopentadienyl or indenyl group, the compounds of formula I may contain either two cyclopentadienyl rings, two indenyl rings or one indenyl and one cyclopentadienyl ring (each of which ring systems may optionally be substituted as described herein). Such compounds may be referred to as "sandwich compounds" as the metal M or metal cation thereof is sandwiched by the two ring systems. The respective cyclopentadienyl and/or indenyl ring systems may be substantially coplanar with respect to each other or they may be tilted with respect to each other (commonly referred to as bent metallocenes).

Alternatively, when n=1 and $L_1$ represents aryl, the compounds of the invention may contain either one cyclopentadienyl or one indenyl ring (each of which ring systems may optionally be substituted as described herein) and one aryl ring which is optionally substituted as defined herein. Suitably, when n=1 and $L_1$ represents aryl then the metal M of the compounds of formula I as defined herein is typically in the form of the metal cation.

In a particularly preferred embodiment of the present invention, in a compound of formula I, n=1, $L_1$ is as defined herein and m=0.

Preferably, when n=1 in the compound of formula I, $L_1$ represents cyclopentadienyl, indenyl or aryl ring each of which rings are optionally substituted by one or more substituents selected from hydrogen, lower alkyl, halo, cyano, nitro, $-OR^{19}$, $-OC(O)R^{20}$, $-C(O)R^{21}$, $C(O)OR^{22}$, $-N(R^{23})R^{24}$, $-C(O)N(R^{25})R^{26}$, $-C(S)(R^{27})R^{28}$ $-SR^{29}$, $-C(O)SR^{30}$, $-CF_3$ or ferrocenyl (by which we mean the cyclopentadienyl, indenyl or aryl ring which $L_1$ may represent is bonded directly to the cyclopentadienyl ring of the ferrocenyl group), wherein $R^{19}$ to $R^{30}$ is as defined herein. More preferably, if the cyclopentadienyl, indenyl or aryl ring which $L_1$ may represent is substituted it is preferably substituted with one or more substituents selected from unsubstituted $C_1$-$C_6$ alkyl, halo, cyano, $-OR^{19}$, $-OC(O)R^{20}$, $-C(O)R^{21}$, $-C(O)OR^{22}$, $-N(R^{23})R^{24}$ where $R^{19}$, $R^{20}$, $R^{21}$, $R^{22}$, $R^{23}$ and $R^{24}$ each independently represent hydrogen or $C_1$-$C_6$ alkyl. Even more preferably, if the cyclopentadienyl, indenyl or aryl ring which $L_1$ may represent is substituted, it is preferably substituted with one or more substituents selected from unsubstituted $C_1$-$C_6$ alkyl.

Preferably, when n=1, $L_1$ represents cyclopentadienyl, indenyl, phenyl or napthyl optionally substituted as defined herein. Preferably, the cyclopentadienyl, indenyl, phenyl or napthyl groups are unsubstituted. More preferably, $L_1$ represents cyclopentadienyl, indenyl or phenyl, each of which rings are unsubstituted. Most preferably, $L_1$ represents unsubstituted cyclopentadienyl. Alternatively, when n=0, the compounds of the invention contain only one cyclopentadienyl or indenyl ring (each of which ring systems may optionally be substituted as described herein). Such compounds may be referred to as "half sandwich compounds". Preferably, when n=0 then m represents 1 to 5 so that the metal M of the compounds of formula I has an 18 electron count. In other words, when metal M of the compounds of formula I is iron, the total number of electrons contributed by the ligands $L_2$ is typically five.

In a particularly preferred alternative embodiment of the present invention, in a compound of formula I, n=0, $L_2$ is as defined herein and m=3 or 4, particularly 3.

Preferably, when n is equal to zero and m is not equal to zero in a compound of formula I, $L_2$ represents one or more ligands each of which are independently selected from lower alkyl, halo, $-CO$, $-P(R^{43})(R^{44})R^{45}$ or $-N(R^{46})(R^{47})R^{48}$. More preferably, $L_2$ represents one or more ligands each of which are independently selected from unsubstituted $C_1$ to $C_4$ alkyl, halo, particularly chloro, $-CO$, $-P(R^{43})(R^{44})R^{45}$ or $-N(R^{46})(R^{47})R^{48}$, wherein $R^{43}$ to $R^{48}$ are independently selected from hydrogen, unsubstituted $C_1$ to $C_6$ alkyl or aryl, such as phenyl.

Suitably, the metal M or metal cation thereof in the compounds of formula I is typically bonded to the cyclopentadienyl ring(s), the cyclopentadienyl moiety of the indenyl ring(s) if present, the aryl ring if present, and/or the ligands $L_2$ if present. Typically, the cyclopentadienyl ring or the cyclopentadienyl moiety of the indenyl ring exhibits a pentahapto bonding mode with the metal; however other bonding modes between the cyclopentadienyl ring or cyclopentadienyl moiety of the indenyl ring and the metal, such as trihapto coordination, are also embraced by the scope of the present invention.

Most preferably, in a compound of formula I, n=1, m=0 and $L_1$ is defined herein, particularly unsubstituted cyclopentadienyl.

By the term "M represents a Group VIB or VIIIB metal" in a compound of formula I we include metals such as Cr, Mo, W, Fe, Co, Ni, Ru and Rh. For the avoidance of doubt, references to Group VIB or VIIIB metals herein include metals of Groups 6, 8, 9 and 10 in the modern periodic table nomenclature.

By the term "metal cation thereof" we mean that the Group VIB or VIIIB metal (M) in the compound of formula I as defined herein has a positive charge. Suitably, the metal cation may be in the form of a salt or may comprise weakly coordinated anions derived from halo, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; perfluororated carboxylic acid such as trichloroacetic acid and trifluoroacetic acid; orthophosphoric acid; phosphonic acid such as benzene phosphonic acid; and acids derived from interactions between Lewis acids and Broensted acids. Other sources which may provide suitable anions include the tetraphenyl borate derivatives.

Preferably M represents a Group VIB or VIIIB metal. In other words the total electron count for the metal M is 18.

Preferably, in the compound of formula I, M represents Cr, Mo, Fe, Co or Ru, or a metal cation thereof. Even more preferably, M represents Cr, Fe, Co or Ru or a metal cation thereof. Most preferably, M is selected from a Group VIIIB metal or metal cation thereof. An especially preferred Group VIIIB metal is Fe. Although the metal M as defined herein may be in a cationic form, preferably it carries essentially no residual charge due to coordination with $L_1$ and/or $L_2$ as defined herein.

The term "aryl" when used herein, includes six- to ten-membered carbocyclic aromatic groups, such as phenyl and naphthyl, which groups are optionally substituted with one or more substituents selected from aryl, lower alkyl (which alkyl group may itself be optionally substituted or terminated as defined below), Het, halo, cyano, nitro, $-OR^{19}$, $-OC(O)R^{20}$, $-C(O)R^{21}$, $-C(O)OR^{22}$, $-N(R^{23})R^{24}$ $-C(O)N(R^{25})R^{26}$, $-SR^{29}$, $-C(O)SR^{30}$ or $-C(S)N(R^{27})R^{28}$ wherein $R^{19}$ to $R^{30}$ each independently represent hydrogen, aryl or lower alkyl (which alkyl group may itself be optionally substituted or terminated as defined below). Preferred aryl groups which k, D, E, $R^1$ to $R^{55}$ and $L_1$ may represent and which adamantyl, 2-phospha-adamantyl, congressyl and lower alkyl may be substituted include phenyl which is optionally substituted with one or more substituents selected from $C_1$-$C_6$ alkyl (which alkyl group itself may be optionally substituted or terminated as defined below), $OR^{19}$, $R^{19}$, halo and $NR^{23}(R^{24})$ where $R^{19}$, $R^{23}$ and $R^{24}$ independently represent hydrogen or lower alkyl. Further preferred aryl groups include phenyl which is optionally substituted with one or more substituents selected from unsubstituted $C_1$-$C_6$ alkyl, $OR^{19}$ wherein $R^{19}$ represents hydrogen or unsubstituted $C_1$-$C_6$ alkyl, particularly unsubstituted $C_1$-$C_6$ alkyl.

The term "Het", when used herein, includes four- to twelve-membered, preferably four- to ten-membered ring systems, which rings contain one or more heteroatoms selected from nitrogen, oxygen, sulfur and mixtures thereof, and which rings contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, aryl or Het, wherein $R^{19}$ to $R^{30}$ each independently represent hydrogen, aryl or lower alkyl, and/or be interrupted by one or more oxygen or sulfur atoms, or by silano or dialkylsilicon groups.

Lower alkyl groups which $R^1$ to $R^{62}$, K, D, E and $L_2$ may represent and which aryl, Het and $L_1$ may be substituted, may, when there is a sufficient number of carbon atoms, be linear or branched, be saturated or unsaturated, be cyclic, acyclic or part cyclic/acyclic, and/or be interrupted by one or more of oxygen or sulfur atoms, or by silano or dialkylsilicon groups, and/or be substituted by one or more substituents selected from halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, aryl or Het wherein $R^{19}$ to $R^{30}$ each independently represent hydrogen, aryl or lower alkyl.

Similarly, the term "lower alkylene" which $A_1$ and $A_2$, and $A_3$, $A_4$ and $A_5$ (when present), represent in a compound of formula I, when used herein, includes $C_{1\ to\ C10}$ groups which can be bonded at two places on the group and is otherwise defined in the same way as "lower alkyl".

Halo groups, which $L_2$ may represent and with which the above-mentioned groups may be substituted or terminated, include fluoro, chloro, bromo and iodo.

Where a compound of the formula (I) contains an alkenyl group, cis (E) and trans (Z) isomerism may also occur. The present invention includes the individual stereoisomers of the compounds of formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the invention.

Suitable Group VIIIB metals or a compound thereof which may be combined with a compound of formula I thereby forming the compounds of the invention include cobalt, nickel, palladium, rhodium and platinum. Preferably, the Group VIIIB metal is palladium or a compound thereof. Suitable compounds of such Group VIIIB metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; perfluororated carboxylic acid such as trichloroacetic acid and trifluoroacetic acid; orthophosphoric acid; phosphonic acid such as benzene phosphonic acid; and acids derived from interactions between Lewis acids and Broensted acids. Other sources, which may provide suitable anions, include the tetraphenyl borate derivatives. Additionally, zero valent palladium with labile ligands e.g. tri(dibenzylideneacetone)dipalladium may be used.

Preferably, zero valent Group VIIIB metals with labile ligands are employed.

Suitably, the compounds of the invention when employed to catalyse the carbonylation of ethylenically unsaturated compounds include a source of anions. Conveniently, the source of anions may be derived by combining a Group VIIIB compound thereof as described in the preceding paragraph with a compound of formula I. Alternatively, or additionally, a separate source of anions as mentioned above may be added to the compounds of the present invention. Preferably, the source of anions are derived from an acid having a pKa less than 4, more preferably a pKa less than 3, as measured at 18° C. in an aqueous solution.

Especially preferred compounds of formula I include those wherein:

(1) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$, wherein each of $R^1$ to $R^{12}$ independently represents unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;

$A_1$ and $A_2$ are the same and represent —$CH_2$—;

K, D and E are the same and represent hydrogen or unsubstituted $C_1$-$C_6$ alkyl, particularly hydrogen;

$Q^1$ and $Q^2$ both represent phosphorus;

M represents Fe;

n=1 and $L_1$ represents cyclopentadienyl, particularly unsubstituted cyclopentadienyl, and m=0.

(2) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;

K represents —$CH_2$-$Q^3(X^5)X^6$ wherein $X^5$ represents $CR^{13}(R^{14})(R^{15})$ and $X^6$ represents $CR^{16}(R^{17})(R^{18})$;

each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;

$A_1$ and $A_2$ are the same and represent —$CH_2$—;

$Q^1$, $Q^2$ and $Q^3$ each represent phosphorus;

D and E are the same and represent hydrogen or unsubstituted $C_1$-$C_6$ alkyl, particularly hydrogen;

M represents Fe;

n=1 and $L_1$ represents cyclopentadienyl, particularly unsubstituted cyclopentadienyl, and m=0.

(3) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;

K represents —$CH_2$-$Q^3(X^5)X^6$ wherein $X^5$ represents $CR^{13}(R^{14})(R^{15})$ and $X^6$ represents $CR^{16}(R^{17})(R^{18})$;

each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;

$A_1$ and $A_2$ are the same and represent —$CH_2$—;

$Q^1$, $Q^2$ and $Q^3$ each represent phosphorus;

D and E together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(4) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$, wherein each of $R^1$ to $R^{12}$ independently represent unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;

$A_1$ and $A_2$ are the same and represent —$CH_2$—;

$Q^1$ and $Q^2$ both represent phosphorus;

K represents hydrogen or $C_1$-$C_6$ alkyl, particularly hydrogen;

D and E together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(5) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;

E represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;

each of $R^1$ to $R^{12}$ and $R^{37}$ to $R^{42}$ independently represent unsubstituted $C_1$-$C_6$ alkyl or trifluoromethyl, particularly where each of $R^1$ to $R^{12}$ and $R^{37}$ to $R^{42}$ is identical, especially where each of $R^1$ to $R^{12}$ and $R^{37}$ to $R^{42}$ represents unsubstituted $C_1$-$C_6$ alkyl, particularly methyl;

$A_1$ and $A_2$ are the same and represent —$CH_2$—;

$Q^1$, $Q^2$ and $Q^5$ each represent phosphorus;

D and K are the same and represent hydrogen or unsubstituted $C_1$-$C_6$ alkyl, particularly hydrogen;

M represents Fe;

n=1 and $L_1$ represents cyclopentadienyl, particularly unsubstituted cyclopentadienyl, and m=0.

(6) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;

K represents —$CH_2$-$Q^3(X^5)X^6$ wherein $X^5$ represents $CR^{13}(R^{14})(R^{15})$ and $X^6$ represents $CR^{16}(R^{17})(R^{18})$;

D represents —$CH_2$-$Q^4(X^7)X^8$ wherein $X^7$ represents $CR^{31}(R^{32})(R^{33})$ and $X^8$ represents $CR^{34}(R^{35})(R^{36})$;

E represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;

each of $R^1$ to $R^{18}$ and $R^{31}$ to $R^{42}$ independently represent unsubstituted $C_1$-$C_6$ alkyl or trifluoromethyl, particularly where each of $R^1$ to $R^{18}$ and $R^{31}$ to $R^{42}$ is identical, especially where each of $R^1$ to $R^{18}$ and $R^{31}$ to $R^{42}$ represents unsubstituted $C_1$-$C_6$ alkyl, particularly methyl;

$A_1$ and $A_2$ are the same and represent —$CH_2$—;

$Q^1$, $Q^2$, $Q^3$, $Q^4$ and $Q^5$ each represent phosphorus

M represents Fe;

n=1 and $L_1$ represents cyclopentadienyl, particularly unsubstituted cyclopentadienyl, and m=0.

(7) $X^1$, $X^2$, $X^3$ and $X^4$ independently represent adamantyl, especially where $X^1$ to $X^4$ represent the same adamantyl group;

$A_1$ and $A_2$ are the same and represent —$CH_2$—;

K, D and E are the same and represent hydrogen or unsubstituted $C_1$-$C_6$ alkyl, particularly hydrogen;

$Q^1$ and $Q^2$ both represent phosphorus;

M represents Fe;

n=1 and $L_1$ represents cyclopentadienyl, particularly unsubstituted cyclopentadienyl, and m=0.

(8) $X^1$, $X^2$, $X^3$ and $X^4$ independently represent adamantyl, especially where $X^1$ to $X^4$ represent the same adamantyl group;

K represents —$CH_2$-$Q^3(X^5)X^6$ wherein $X^5$ and $X^6$ independently represent adamantyl, especially where $X^1$ to $X^6$ represent the same adamantyl group;

$A_1$ and $A_2$ are the same and represent —$CH_2$—;

$Q^1$, $Q^2$ and $Q^3$ each represent phosphorus;

D and E are the same and represent hydrogen or unsubstituted $C_1$-$C_6$ alkyl, particularly hydrogen;

M represents Fe;

n=1 and $L_1$ represents cyclopentadienyl, particularly unsubstituted cyclopentadienyl, and m=0.

(9) $X^1$, $X^2$, $X^3$ and $X^4$ independently represent adamantyl, especially where $X^1$ to $X^4$ represent the same adamantyl group;

K represents —$CH_2$-$Q^3(X^5)X^6$ wherein $X^5$ and $X^6$ independently represent adamantyl, especially where $X^1$ to $X^6$ represent the same adamantyl group;

$A_1$ and $A_2$ are the same and represent —$CH_2$—;

$Q^1$, $Q^2$ and $Q^3$ each represent phosphorus;

D and E together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(10) $X^1$, $X^2$, $X^3$ and $X^4$ independently represent adamantyl, especially where $X^1$ to $X^4$ represent the same adamantyl group;

$A_1$ and $A_2$ are the same and represent —$CH_2$—;

$Q^1$ and $Q^2$ both represent phosphorus;

K represents hydrogen or unsubstituted $C_1$-$C_6$ alkyl, particularly hydrogen;

D and E together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(11) $X^1$, $X^2$, $X^3$ and $X^4$ independently represent adamantyl;

K represents —$CH_2$-$Q^3(X^5)X^6$ wherein $X^5$ and $X^6$ independently represent adamantyl;

D represents —CH$_2$-Q$^4$(X$^7$)X$^8$ wherein X$^7$ and X$^8$ independently represents adamantyl;
E represents —CH$_2$-Q$^5$(X$^9$)X$^{10}$ wherein X$^9$ and X$^{10}$ independently represents adamantyl, especially where X$^1$ to X$^{10}$ represent the same adamantyl group;
A$_1$ and A$_2$ are the same and represent —CH$_2$—;
Q$^1$, Q$^2$, Q$^3$, Q$^4$ and Q$^5$ each represent phosphorus;
M represents Fe;
n=1 and L$_1$ represents cyclopentadienyl, particularly unsubstituted cyclopentadienyl, and m=0.

(12) X$^1$ and X$^2$ together with Q$^2$ to which they are attached represents 2-phospha-adamantyl;
X$^3$ and X$^4$ together with Q$^1$ to which they are attached represents 2-phospha-adamantyl;
A$_1$ and A$_2$ are the same and represent —CH$_2$—;
K, D and E are the same and represent hydrogen or unsubstituted C$_1$-C$_6$ alkyl, particularly hydrogen;
Q$^1$ and Q$^2$ both represent phosphorus;
M represents Fe;
n=1 and L$_1$ represents cyclopentadienyl, particularly unsubstituted cyclopentadienyl, and m=0.

(13) X$^1$ and X$^2$ together with Q$^2$ to which they are attached represents 2-phospha-adamantyl;
X$^3$ and X$^4$ together with Q$^1$ to which they are attached represents 2-phospha-adamantyl;
K represents —CH$_2$-Q$^3$(X$^5$)X$^6$ wherein X$^5$ and X$^6$ together with Q$^3$ to which they are attached represents 2-phospha-adamantyl;
A$_1$ and A$_2$ are the same and represent —CH$_2$—;
Q$^1$, Q$^2$ and Q$^3$ each represent phosphorus;
D and E are the same and represent hydrogen or unsubstituted C$_1$-C$_6$ alkyl, particularly hydrogen;
M represents Fe;
n=1 and L$_1$ represents cyclopentadienyl, particularly unsubstituted cyclopentadienyl, and m=0.

(14) X$^1$ and X$^2$ together with Q$^2$ to which they are attached represents 2-phospha-adamantyl;
X$^3$ and X$^4$ together with Q$^1$ to which they are attached represents 2-phospha-adamantyl;
K represents —CH$_2$-Q$^3$(X$^5$)X$^6$ wherein X$^5$ and X$^6$ together with Q$^3$ to which they are attached represents 2-phospha-adamantyl;
A$_1$ and A$_2$ are the same and represent —CH$_2$—;
Q$^1$, Q$^2$ and Q$^3$ each represent phosphorus;
D and E together with the carbon atoms of the cyclopentadienyl ring to which they are attached form an unsubstituted phenyl ring;
M represents Fe;
n=1 and L$_1$ represents cyclopentadienyl, particularly unsubstituted cyclopentadienyl, and m=0.

(15) X$^1$ and X$^2$ together with Q$^2$ to which they are attached represents 2-phospha-adamantyl;
X$^3$ and X$^4$ together with Q$^1$ to which they are attached represents 2-phospha-adamantyl;
A$_1$ and A$_2$ are the same and represent —CH$_2$—;
Q$^1$ and Q$^2$ both represent phosphorus;
K represents hydrogen or unsubstituted C$_1$-C$_6$ alkyl, particularly hydrogen;
D and E together with the carbon atoms of the cyclopentadienyl ring to which they are attached form an unsubstituted phenyl ring;
M represents Fe;
n=1 and L$_1$ represents cyclopentadienyl, particularly unsubstituted cyclopentadienyl, and m=0.

(16) X$^1$ and X$^2$ together with Q$^2$ to which they are attached represents 2-phospha-adamantyl;
X$^3$ and X$^4$ together with Q$^1$ to which they are attached represents 2-phospha-adamantyl;
K represents —CH$_2$-Q$^3$(X$^5$)X$^6$ wherein X$^5$ and X$^6$ together with Q$^3$ to which they are attached represents 2-phospha-adamantyl;
D represents —CH$_2$-Q$^4$(X$^7$)X$^8$ wherein X$^7$ and X$^8$ together with Q$^4$ to which they are attached represents 2-phospha-adamantyl;
E represents —CH$_2$-Q$^5$(X$^9$)X$^{10}$ wherein X$^9$ and X$^{10}$ together with Q$^5$ to which they are attached represents 2-phospha-adamantyl;
A$_1$ and A$_2$ are the same and represent —CH$_2$—;
Q$^1$, Q$^2$, Q$^3$, Q$^4$ and Q$^5$ each represent phosphorus
M represents Fe;
n=1 and L$_1$ represents cyclopentadienyl, particularly unsubstituted cyclopentadienyl, and m=0.

(17) X$^1$ and X$^2$ together with Q$^2$ to which they are attached form a ring system of formula Ia, X$^3$ and X$^4$ together with Q$^1$ to which they are attached form a ring system of formula Ib, wherein Y$^1$ and Y$^2$ both represent oxygen, R$^{50}$ to R$^{53}$ are independently selected from unsubstituted C$_1$-C$_6$ alkyl or CF$_3$, and R$^{49}$ and R$^{54}$ represent hydrogen;
A$_1$ and A$_2$ are the same and represent —CH$_2$—;
K, D and E are the same and represent hydrogen or unsubstituted C$_1$-C$_6$ alkyl, particularly hydrogen;
Q$^1$ and Q$^2$ both represent phosphorus;
M represents Fe;
n=1 and L$_1$ represents cyclopentadienyl, particularly unsubstituted cyclopentadienyl (referred to as puc) and m=0.

(18) X$^1$ and X$^2$ together with Q$^2$ to which they are attached form a ring system of formula Ia, X$^3$ and X$^4$ together with Q$^1$ to which they are attached form a ring is system of formula Ib, wherein Y$^1$ and Y$^2$ both represent oxygen, R$^{50}$ to R$^{53}$ are independently selected from unsubstituted C$_1$-C$_6$ alkyl or CF$_3$, and R$^{49}$ and R$^{54}$ represent hydrogen;
K represents —CH$_2$-Q$^3$(X$^5$)X$^6$ wherein X$^5$ and X$^6$ together with Q$^3$ to which they are attached form a ring system of formula Ic, wherein Y$^3$ represents oxygen, R$^{50}$ to R$^{53}$ are independently selected from hydrogen, unsubstituted C$_1$-C$_6$ alkyl or CF$_3$ and R$^{49}$ and R$^{54}$ represent hydrogen;
A$_1$ and A$_2$ are the same and represent —CH$_2$—;
Q$^1$, Q$^2$ and Q$^3$ each represent phosphorus;
D and E are the same and represent hydrogen or C$_1$-C$_6$ alkyl, particularly hydrogen;
M represents Fe;
n=1 and L$_1$ represents cyclopentadienyl, particularly unsubstituted cyclopentadienyl, and m=0.

(19) X$^1$ and X$^2$ together with Q$^2$ to which they are attached form a ring system of formula Ia, X$^3$ and X$^4$ together with Q$^1$ to which they are attached form a ring system of formula Ib, wherein. Y$^1$ and Y$^2$ both represent oxygen, R$^{50}$ to R$^{53}$ are independently selected from unsubstituted C$_1$-C$_6$ alkyl or CF$_3$, and R$^{49}$ and R$^{54}$ represent hydrogen;
K represents —CH$_2$-Q$^3$(X$^5$)X$^6$ wherein X$^5$ and X$^6$ together with Q$^3$ to which they are attached form a ring system of formula Ic, wherein Y$^3$ represents oxygen, R$^{50}$ to R$^{53}$ are independently selected from unsubstituted C$_1$-C$_6$ alkyl or CF$_3$, and R$^{49}$ and R$^{54}$ represent hydrogen;
A$_1$ and A$_2$ are the same and represent —CH$_2$—;
Q$^1$, Q$^2$ and Q$^3$ each represent phosphorus;
D and E together with the carbon atoms of the cyclopentadienyl ring to which they are attached form an unsubstituted phenyl ring;
M represents Fe;
n=1 and L$_1$ represents cyclopentadienyl, particularly unsubstituted cyclopentadienyl, and m=0.

(20) $X^1$ and $X^2$ together with $Q^2$ to which they are attached form a ring system of formula Ia, $X^3$ and $X^4$ together with $Q^1$ to which they are attached form a ring system of formula Ib, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
  $A_1$ and $A_2$ are the same and represent —$CH_2$—;
  $Q^1$ and $Q^2$ both represent phosphorus;
  K represents hydrogen or unsubstituted $C_1$-$C_6$ alkyl, particularly hydrogen;
  D and E together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(21) $X^1$ and $X^2$ together with $Q^2$ to which they are attached form a ring system of formula Ia, $X^3$ and $X^4$ together with $Q^1$ to which they are attached form a ring system of formula Ib, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
  K represents —$CH_2$-$Q^3(X^5)X^6$ wherein $X^5$ and $X^6$ together with $Q^3$ to which they are attached form a ring system of formula Ic, wherein $Y^3$ represents oxygen, $R^{50}$ to $R^{53}$ are independently selected from unsubstituted $C_3$-$C_6$ alkyl or $CF_3$, and $R^{49}$ and $R^{54}$ represent hydrogen;
  D represents —$CH_2$-$Q^4(X^7)X^8$ wherein $X^7$ and $X^8$ together with $Q^4$ to which they are attached form a ring system of formula Ic, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;
  E represents —$CH_2$-$Q^5(X^9)X^{10}$ wherein $X^9$ and $X^{10}$ together with $Q^5$ to which they are attached form a ring system of formula Ie, wherein $Y^5$ represents oxygen, and $R^{50}$ to $R^{53}$ are independently selected from unsubstituted $C_1$-$C_6$ alkyl or $CF_3$, and $R^{49}$ and $R^{54}$ represent hydrogen;
  $A_1$ and $A_2$ are the same and represent —$CH_2$—;
  $Q^1$, $Q^2$, $Q^3$, $Q^4$ and $Q^5$ each represent phosphorus,
  M represents Fe;
  n=1 and $L_1$ represents cyclopentadienyl; particularly unsubstituted cyclopentadienyl, and m=0.
(22) $X^1$, $X^2$, $X^3$ and $X^4$ independently represent congressyl, especially where $X^1$ to $X^4$ represent the same congressyl group;
  $A_1$ and $A_2$ are the same and represent —$CH_2$—;
  K, D and E are the same and represent hydrogen or unsubstituted $C_1$-$C_6$ alkyl, particularly hydrogen;
  $Q^1$ and $Q^2$ both represent phosphorus;
  M represents Fe;
  n=1 and $L_1$ represents cyclopentadienyl, particularly unsubstituted cyclopentadienyl, and m=0.
(23) $X^1$, $X^2$, $X^3$ and $X^4$ independently represent congressyl, especially where $X^1$ to $X^4$ represent the same congressyl group;
  K represents —$CH_2$-$Q^3(X^5)X^6$ wherein $X^5$ and $X^6$ independently represent congressyl, especially where $X^1$ to $X^6$ represent the same congressyl group;
  $A_1$ and $A_2$ are the same and represent —$CH_2$—;
  $Q^1$, $Q^2$ and $Q^3$ each represent phosphorus;
  D and E are the same and represent hydrogen or unsubstituted $C_1$-$C_6$ alkyl, particularly hydrogen;
  M represents Fe;
  n=1 and $L_1$ represents cyclopentadienyl, particularly unsubstituted cyclopentadienyl, and m=0.
(24) $X^1$, $X^2$, $X^3$ and $X^4$ independently represent congressyl, especially where $X^1$ to $X^4$ represent the same congressyl group;
  K represents —$CH_2$-$Q^3(X^5)X^6$ wherein $X^5$ and $X^6$ independently represent congressyl, especially where $X^1$ to $X^6$ represent the same congressyl group;
  $A_1$ and $A_2$ are the same and represent —$CH_2$—;
  $Q^1$, $Q^2$ and $Q^3$ each represent phosphorus;
  D and E together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(25) $X^1$, $X^2$, $X^3$ and $X^4$ independently represent congressyl, especially where $X^1$ to $X^4$ represent the same congressyl group;
  $A_1$ and $A_2$ are the same and represent —$CH_2$—;
  $Q^1$ and $Q^2$ both represent phosphorus;
  K represents hydrogen or unsubstituted $C_1$-$C_6$ alkyl, particularly hydrogen;
  D and E together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(26) $X^1$, $X^2$, $X^3$ and $X^4$ independently represent congressyl;
  K represents —$CH_2$-$Q^3(X^5)X^6$ wherein $X^5$ and $X^6$ independently represent congressyl;
  D represents —$CH_2$-$Q^4(X^7)X^8$ wherein $X^7$ and $X^8$ independently represents congressyl;
  E represents —$CH_2$-$Q^5(X^9)X^{10}$ wherein $X^9$ and $X^{10}$ independently represents congressyl, especially where $X^1$ to $X^{10}$ represent the same congressyl group;
  $A_1$ and $A_2$ are the same and represent —$CH_2$—;
  $Q^1$, $Q^2$, $Q^3$, $Q^4$ and $Q^5$ each represent phosphorus;
  M represents Fe;
  n=1 and $L_1$ represents cyclopentadienyl, particularly unsubstituted cyclopentadienyl, and m=0.
(27) $X^1$ and $X^3$ independently represent adamantyl, especially where $X^1$ and $X^3$ represent the same adamantyl group;
  $X^2$ represents $CR^4(R^5)(R^6)$ and $X^4$ represents $CR^{10}(R^{11})(R^{12})$ wherein each of $R^4$, $R^5$, $R^6$, $R^{10}$, $R^{11}$ and $R^{12}$ independently represent $C_1$-$C_6$ alkyl or trifluoromethyl, particularly where each of $R^4$ to $R^6$ and $R^{10}$ to $R^{12}$ is identical, especially where each of $R^4$ to $R^6$ and $R^{10}$ to $R^{12}$ represents unsubstituted $C_1$-$C_6$ alkyl, particularly methyl;
  $A_1$ and $A_2$ are the same and represent —$CH_2$—;
  K, D and E are the same and represent hydrogen or unsubstituted $C_1$-$C_6$ alkyl, particularly hydrogen;
  $Q^1$ and $Q^2$ both represent phosphorus;
  M represents Fe;
  n=1 and $L_1$ represents cyclopentadienyl, particularly unsubstituted cyclopentadienyl, and m=0.
(28) $X^1$ and $X^3$ independently represent adamantyl, especially where $X^1$ and $X^3$ represent the same adamantyl group;
  K represents —$CH_2$-$Q^3(X^5)X^6$ wherein $X^5$ represents adamantyl, especially where $X^1$, $X^3$ and $X^5$ represent the same adamantyl group;

$X^2$ represents $CR^4(R^5)(R^6)$ $X^4$ represents $CR^{10}(R^{11})(R^{12})$, $X^6$ represents $CR^{16}(R^{17})(R^{18})$, wherein each of $R^4$ to $R^6$, $R^{10}$ to $R^{12}$ and $R^{16}$ to $R^{18}$ independently represent unsubstituted $C_1$-$C_6$ alkyl or trifluoromethyl, particularly where each of $R^4$ to $R^6$, $R^{10}$ to $R^{12}$, and $R^{16}$ to $R^{18}$ is identical, especially where each of $R^4$ to $R^6$, $R^{10}$ to $R^{12}$ and $R^{16}$ to $R^{18}$ represents unsubstituted $C_1$-$C_6$ alkyl, particularly methyl;

$A_1$ and $A_2$ are the same and represent —$CH_2$—;

$Q^1$, $Q^2$ and $Q^3$ each represent phosphorus;

D and E are the same and represent hydrogen or unsubstituted $C_1$-$C_6$ alkyl, particularly hydrogen;

M represents Fe;

n=1 and $L_1$ represents cyclopentadienyl, particularly unsubstituted cyclopentadienyl, and m=0.

(29) $X^1$ and $X^3$ independently represent adamantyl, especially where $X^1$ and $X^3$ represent the same adamantyl group;

K represents —$CH_2$-$Q^3(X^5)X^6$ wherein $X^5$ represents adamantyl, especially where $X^1$, $X^3$ and $X^5$ represent the same adamantyl group;

$X^2$ represents $CR^4(R^5)(R^6)$, $X^4$ represents $CR^{10}(R^{11})(R^{12})$, $X^6$ represents $CR^{16}(R^{17})(R^{18})$, wherein each of $R^4$ to $R^6$, $R^{10}$ to $R^{12}$ and $R^{16}$ to $R^{18}$ independently represent unsubstituted $C_1$-$C_6$ alkyl or trifluoromethyl, particularly where each of $R^4$ to $R^6$, $R^{10}$ to $R^{12}$, and $R^{16}$ to $R^{18}$ is identical, especially where each of $R^4$ to $R^6$, $R^{10}$ to $R^{12}$ and $R^{16}$ to $R^{18}$ represents unsubstituted $C_1$-$C_6$ alkyl, particularly methyl;

$A_1$ and $A_2$ are the same and represent —$CH_2$—;

$Q^1$, $Q^2$ and $Q^3$ each represent phosphorus;

D and E together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(30) $X^1$ and $X^3$ independently represent adamantyl, especially where $X^1$ and $X^3$ represent the same adamantyl group;

$X^2$ represents $CR^4(R^5)(R^6)$ and $X^4$ represents $CR^{10}(R^{11})(R^{12})$ wherein each of $R^4$, $R^5$, $R^6$, $R^{10}$, $R^{11}$ and $R^{12}$ independently represent $C_1$-$C_6$ alkyl or trifluoromethyl, particularly where each of $R^4$ to $R^6$ and $R^{10}$ to $R^{12}$ is identical, especially where each of $R^4$ to $R^6$ and $R^{10}$ to $R^{12}$ represents unsubstituted $C_1$-$C_6$ alkyl, particularly methyl;

$A_1$ and $A_2$ are the same and represent —$CH_2$—;

$Q^1$ and $Q^2$ both represent phosphorus;

K represents hydrogen or unsubstituted $C_1$-$C_6$ alkyl, particularly hydrogen;

D and E together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

According to a second aspect, the present invention provides a process for preparing the compounds of the invention comprising combining (a) a Group VIIIB metal or compound thereof, as defined herein; with (b) a compound of formula I as defined herein.

Conveniently, the compounds of the invention may be obtained by dissolving the Group VIIIB metal or compound thereof as defined herein in a suitable solvent such as the ultimate end product of the carbonylation reaction, for example methylpropanoate where the ethylenically unsaturated compound to be carbonylated is ethene in the presence of methanol or methylnonanoate where it is intended to carbonylate octene in the presence of methanol. Preferably, the reactants are mixed at room temperature under an inert atmosphere (e.g. under nitrogen). The molar ratio of the compound of formula I (referred to as (b)) to the Group VIIIB metal or compound thereof (referred to as (a)) is preferably in the range of 1:1 to 5:1, more preferably in the range of 1:1 to 3:1, most preferably in the range of 1:1 to 1:1.25. Conveniently, the possibility of applying these low molar ratios is advantageous, as it avoids the use of an excess of the compound of formula I and hence minimises the consumption of these usually expensive compounds. Suitably, the compounds of the invention are prepared in a separate step preceding their use in-situ in the carbonylation reaction of an ethylenically unsaturated compound. As mentioned previously, the compounds of the invention may include additional anions derivable from the Group VIIIB compound thereof, if one is employed, and/or by the addition of a separate source of anions. If a separate source of anions is employed these may be added to the compounds of the invention prior to use in the carbonylation reaction. Alternatively, or additionally, a separate source of anions may be added to the carbonylation reaction.

According to a third aspect, the present invention provides a compound of formula I as defined herein.

According to a fourth aspect, the present invention provides a process for the preparation of a compound of formula I, which comprises the reaction of a compound of formula II wherein $A_1$, $A_2$, K, D, E, M, $L_1$, $L_2$, n and m are as defined for a compound of formula I, and $LG_1$ and $LG_2$ represent suitable leaving groups,

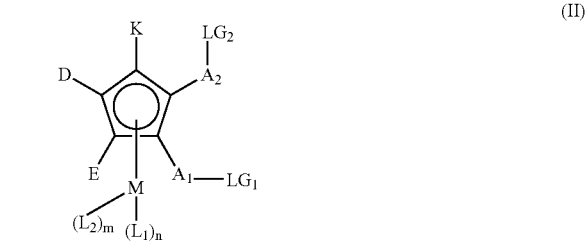

with a compound of formula IIIa and IIIb

$HQ^2(X^1)X^2$         (IIIa)

$HQ^1(X^3)X^4$         (IIIb)

wherein $X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form a 2-phospha-adamantyl group, or $X^1$ and $X^2$ together with $Q^2$ to which they are attached form a ring system of formula Ia;

wherein $X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form a 2-phospha-adamantyl group, or $X^3$ and $X^4$ together with $Q^1$ to which they are attached form a ring system of formula Ib;

$R^1$ to $R^{12}$, adamantyl, congressyl, $Q^1$ and $Q^2$, 2-phospha-adamantyl, and the ring systems of formula Ia and Ib are as defined for a compound of formula I.

Suitable leaving groups which $LG_1$ and $LG_2$ may independently represent include groups which are readily displaced by nucleophilic attack by the phosphine, arsine or stibene derivatives IIIa and IIIb. Examples of such groups include halo, particularly bromo and iodo, —$NR^{23}R^{24}$ where $R^{23}$ and $R^{24}$ both represent lower alkyl, particularly methyl, and hyroxyl whether in a protonated form or not. Preferably, $LG_1$ and $LG_2$ each independently represent —$NMe_2$ or hydroxyl. Most preferably, both $LG_1$ and $LG_2$ represent —$NMe_2$, or $LG_1$ and $LG_2$ represent $NMe_2$ or hydroxyl, respectively.

The reaction may be accomplished using methods which are well known to those skilled in the art. For example, the reaction may be accomplished by heating a solution of a compound of formula II with a compound of formula IIIa and IIIb in anhydrous acetic acid at a temperature between 70 to 90° C., preferably approximately 80° C. under an inert atmosphere, such as a nitrogen atmosphere.

Preferably, when the compound of formula IIIa represents $HQ^2(CR^1(R^2)(R^3))CR^4(R^5)(R^6)$ then the compound of formula IIIb represents $HQ^1(CR^7(R^8)(R^9))CR^{10}(R^{11})(R^{12})$ wherein $Q^1$ is the same as $Q^2$ and $R^1$ is the same as $R^7$, $R^2$ is the same as $R^8$, $R^3$ is the same as $R^9$, $R^4$ is the same as $R^{10}$, $R^5$ is the same as $R^{11}$, and $R^6$ is the same as $R^{12}$.

Preferably, when the compound of formula IIIa represents $HQ^2(X^1)X^2$ wherein $X^1$ and $X^2$ independently represent adamantyl, then the compound of formula IIIb represents $HQ^1(X^3)X^4$ wherein $X^3$ and $X^4$ independently represent adamantyl. More preferably, $X^1$ represents the same adamantyl group as $X^3$, $X^2$ represents the same adamantyl group as $X^4$, and $Q^1$ is the same as $Q^2$.

Preferably, when the compound of formula IIIa represents $HQ^2(X^1)X^2$ wherein $X^1$ and $X^2$ independently represent congressyl, then the compound of formula IIIb represents $HQ^1(X^3)X^4$ wherein $X^3$ and $X^4$ independently represent congressyl. More preferably, $X^1$ represents the same congressyl group as $X^3$, $X^2$ represents the same congressyl group as $X^4$, and $Q^1$ is the same as $Q^2$.

Preferably, when the compound of formula IIIa represents $HQ^2(X^1)X^2$ wherein $X^1$ and $X^2$ together with $Q^2$ to which they are attached form a 2-phospha-adamantyl group, then the compound of formula IIIb represents $HQ^1(X^3)X^4$ wherein $X^3$ and $X^4$ together with $Q^1$ to which they are attached form a 2-phospha-adamantyl group. More preferably, $X^1$ and $X^2$ together with $Q^2$ forms the same 2-phospha-adamantyl group formed by the combination of $X^3$ and $X^4$ together with $Q^1$.

Preferably, when the compound of formula IIIa represents $HQ^2(X^1)X^2$ wherein $X^1$ and $X^2$ together with $Q^2$ to which they are attached form a ring system of formula Ia, then the compound of formula IIIb represents $HQ^1(X^3)X^4$ where $X^3$ and $X^4$ together with $Q^1$ to which they are attached form a ring system of formula Ib. Preferably, the ring system of formula Ia is the same as the ring system of formula Ib.

Most preferably, the compound of formula IIIa is identical to the compound of formula IIIb.

A compound of formula II, where $LG_2$ represents hydroxyl or $NR^{23}R^{24}$, may be prepared by reaction of a compound of formula IV, wherein $A_1$, $LG_1$, K, D, E, M, $L_1$, $L_2$, n and m are as defined for a compound of formula II, and Li represents lithium,

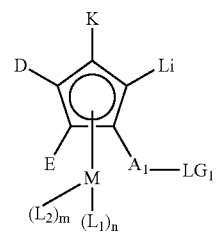

with a compound of formula Va $$A_2=LG_2 \qquad (Va)$$

wherein $A_2$ is as defined for a compound of formula II and $LG_2$ represents oxygen (thereby forming a hydroxyl derivative following reaction with compound IV) or $NR^{23}R^{24}$. Preferably, in a compound of formula Va, $A_2$ represents methylene and $LG_2$ represents $NMe_2$. For example, a compound of formula Va may represent Eschenmosers salt I$^-$CH$_2$N$^+$Me$_2$ (see Glidewell C, Journal of Organometallic Chemistry, 527, (1997), p. 259-261).

Alternatively, in a compound of formula Va, $A_2$ represents methylene and $LG_2$ represents oxygen. For example, a compound of formula Va may represent formaldehyde, which for practical purposes may be paraformaldehyde.

The reaction may be carried out using methods which are well known to those skilled in the art. For example, the reaction may be accomplished by stirring a solution of the compound of formula IV and Va in an appropriate solvent, such as diethyl ether, at room temperature.

Preferably, in a compound of formula IV, $LG_1$ does not represent hydroxyl, as the hydroxyl functionality will typically have to be protected prior to ortho-lithiating the precursor compound (compound VI below) to the compound of formula IV. Preferably, in a compound of formula IV, $LG_1$ represents $NR^{23}R^{24}$, most preferably $LG_1$ represents $NMe_2$.

A compound of formula IV may be prepared by ortho-lithiation of a compound of formula VI, wherein $A_1$, $LG_1$, K, D, E, M, $L_1$, $L_2$, n and m are as defined for a compound of formula IV,

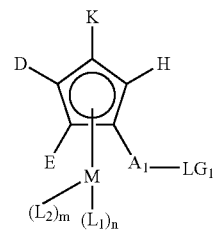

by reaction with an alkyl lithium (e.g. n-butyl lithium).

Preferably, in a compound of formula VI, $LG_1$ does not represent hydroxyl, as the hydroxyl functionality will typically have to be protected prior to performing the ortho-lithiation reaction. Preferably, in a compound of formula VI, $LG_1$ represents $NR^{23}R^{24}$, most preferably $LG_1$ represents $NMe_2$.

Typically, the ortho-lithiation reaction of compounds of formula VI with an alkyl lithium is performed in an inert solvent, for example tetrahydrofuran or hexane, at low temperatures (e.g. −78° C.), under a nitrogen atmosphere.

A compound of formula VI, where $LG_1$ represents hydroxyl or $NR^{23}R^{24}$, may be prepared from a compound of formula VII wherein K, D, E, M, $L_1$, $L_2$, n and m are as defined for a compound of formula VI and Li represents lithium

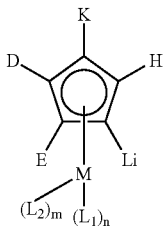

(VII)

by reaction with a compound of formula Vb $$A_1=LG_1 \quad \text{(Vb)}$$

wherein $A_1$ is as defined for a compound of formula VI and $LG_1$ represents oxygen (thereby forming a hydroxyl derivative following reaction with compound VII) or $NR^{23}R^{24}$. Preferably, $LG_1$ represents $NR^{23}R^{24}$, especially $NMe_2$. In other words, a compound of formula Vb is preferably Eschenmosers salt. The reaction may be accomplished using similar conditions as described for the preparation of a compound of formula II above.

Similarly, a compound of formula VII may be prepared by lithiation of a compound of formula VIII

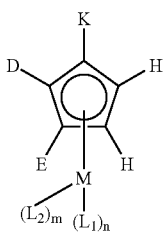

(VIII)

wherein K, D, E, M, $L_1$, $L_2$, n and m are as defined for a compound of formula VII.

Suitably, a compound of formula I wherein K represents $-A_3-Q^3(X^5)X^6$ may be prepared from a compound of formula IX wherein $A_1$, $A_2$, $A_3$, D, E, M, $L_1$, $L_2$, n and m are as defined for a compound of formula I, and $LG_1$, $LG_2$ and $LG_3$ represent suitable leaving groups as defined herein,

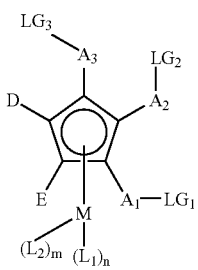

(IX)

by reaction with a compound of formula IIIa and IIIb as defined herein, and a compound of formula IIIc $$HQ^3(X^5)X^6 \quad \text{(IIIc)}$$

wherein $X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ form a 2-phospha-adamantyl group, or $X^5$ and $X^6$ together with $Q^3$ to which they are attached form a ring system of formula Ic; and $R^{13}$ to $R^{18}$, congressyl, adamantyl, $Q^3$, 2-phospha-adamantyl, and the ring system of formula Ic are as defined for a compound of formula I.

Preferably, when the compound of formula IIIa represents $HQ^2(CR^1(R^2)(R^3))CR^4(R^5)(R^6)$, then the compound of formula is IIIb represents $HQ^1(CR^7(R^8)(R^9))CR^{10}(R^{11})(R^{12})$ and the compound of formula IIIc represents $HQ^3(CR^{13}(R^{14})(R^{15}))CR^{17}(R^{18})(R^{19})$, $Q^1$ is the same as $Q^2$ and $Q^3$, $R^1$ is the same as $R^7$ and $R^{13}$, $R^2$ is the same as $R^8$ and $R^{14}$, $R^3$ is the same as $R^9$ and $R^{15}$, $R^4$ is the same as $R^{10}$ and $R^{16}$, $R^5$ is the same as $R^{11}$ and $R^{17}$, and $R^6$ is the same as $R^{12}$ and $R^{18}$.

Preferably, when $X^1$ and $X^2$ in the compound of formula IIIa independently represents adamantyl, then $X^3$ and $X^4$ in the compound of formula IIIb independently represent adamantyl, and $X^5$ and $X^6$ in the compound of formula IIIc independently represent adamantyl. Most preferably, $X^1$ to $X^6$ represent the same adamantyl group.

Preferably, when $X^1$ and $X^2$ in the compound of formula IIIa independently represents congressyl, then $X^3$ and $X^4$ in the compound of formula IIIb independently represent congressyl, and $X^5$ and $X^6$ in the compound of formula IIIc independently represent congressyl. Most preferably, $X^1$ to $X^6$ represent the same congressyl group.

Preferably, when $X^1$ and $X^2$ together with $Q^2$ to which they are attached in the compound of formula IIIa form a 2-phospha-adamantyl group, then $X^3$ and $X^4$ together with $Q^1$ in the compound of formula IIIb, and $X^5$ and $X^6$ together with $Q^3$ in the compound of formula IIIc both form a 2-phospha-adamantyl group.

Preferably, when $X^1$ and $X^2$ together with $Q^2$ to which they are attached form a ring system of formula Ia, then $X^3$ and $X^4$ together with $Q^1$ to which they are attached in the compound of IIIb forms a ring system of formula Ib, and $X^5$ and $X^6$ together with $Q^3$ to which they are attached in the compound IIIc forms a ring system of formula Ic.

Most preferably, the compounds of formula IIIa, IIIb and IIIc are identical.

Suitably, $LG_3$ represents a leaving group as defined herein in respect of $LG_1$ and $LG_2$. Preferably, $LG_3$ represents $NR^{23}R^{24}$ or hydroxyl. Most preferably, $LG_3$ represents $NMe_2$, particularly when both $LG_1$ and $LG_2$ also represent $NMe_2$.

Similarly, the compound of formula IX, where $LG_3$ represents hydroxyl or $NR^{23}R^{24}$, may be prepared by ortho-lithiation of a compound of formula II wherein $A_1$, $A_2$, $LG_1$, $LG_2$, D, E, M, $L_1$, $L_2$, n and m are as defined for a compound of formula II and K represents hydrogen, followed by reaction with a compound of formula Vc $$A_3=LG_3 \quad \text{(Vc)}$$

wherein $A_3$ is as defined for a compound of formula IX and $LG_3$ represents oxygen or $NR^{23}R^{24}$. Preferably, when employing a compound of formula II to synthesise a compound of formula IX, $LG_1$ and $LG_2$ do not represent hydroxyl, as the hydroxyl functionality will typically have to be protected prior to performing the ortho-lithiation reaction. Preferably, both $LG_1$ and $LG_2$ represent $NR^{23}R^{24}$, most preferably both $LG_1$ and $LG_2$ represent $NMe_2$.

Similarly, a compound of formula I wherein K represents $-A_3-Q^3(X^5)X^6$ and D represents $-A_4-Q^4(X^7)X^8$ may be prepared from a compound of formula IX wherein $A_1$, $A_2$, $A_3$, $LG_1$, $LG_2$, $LG_3$, E, M, $L_1$, $L_2$, n and m are as defined for a compound of formula IX and D represents hydrogen, by sequential ortho-lithiation and reaction with a compound of formula V(d)

$$A_4=LG_4 \quad (Vd)$$

wherein $A_4$ is as defined for a compound of formula I and $LG_4$ represents oxygen or $NR^{23}R^{24}$ as defined herein, to form a compound of formula X followed by reaction of the resultant compound of formula X with a phosphine, arsine or stilbene derivative of formula IIIa, IIIb, IIIc as defined herein and a compound of formula IIId $$HQ^4(X^7)X^8 \quad (IIId)$$

wherein $X^7$ represents $CR^{31}(R^{32})R^{33}$, congressyl or adamantyl, $X^8$ represents $CR^{34}(R^{35})(R^{36})$, congressyl or adamantyl, or $X^7$ and $X^8$ together with $Q^4$ form a 2-phospha-adamantyl group, or $X^7$ and $X^8$ together with $Q^4$ forms a ring system of formula Id, and $R^{31}$ to $R^{36}$, adamantyl, $Q^4$, 2-phospha-adamantyl, and the ring system of formula Id are as defined for a compound of formula I.

Preferably, when the compound of formula IIIa represents $HQ^2(CR^1(R^2)(R^3))CR^4(R^5)(R^6)$, then the compound of formula IIIb represents $HQ^1(CR^7(R^8)(R^9))CR^{10}(R^{11})(R^{12})$, the compound of formula IIIc represents $HQ^3(CR^{13}(R^{14})(R^{15}))CR^{16}(R^{17})(R^{18})$ and the compound of formula IIId represents $HQ^4(CR^{31}(R^{32})(R^{33}))CR^{34}(R^{35})(R^{36})$, and $Q^1$ is the same as $Q^2$, $Q^3$ and $Q^4$, $R^1$ is the same as $R^7$, $R^{13}$ and $R^{31}$, $R^2$ is the same as $R^8$, $R^{14}$ and $R^{32}$, $R^3$ is the same as $R^9$, $R^{15}$ and $R^{33}$, $R^4$ is the same as $R^{10}$, $R^{16}$ and $R^{34}$, $R^5$ is the same as $R^{11}$, $R^{17}$ and $R^{35}$, and $R^6$ is the same as $R^{12}$, $R^{18}$ and $R^{36}$.

Preferably, when $X^1$ and $X^2$ in the compound of formula IIIa independently represent adamantyl, then $X^3$ and $X^4$ in the compound of formula IIIb independently represent adamantyl, $X^5$ and $X^6$ in the compound of formula IIIc independently represent adamantyl, and $X^7$ and $X^8$ in the compound of formula IIId independently represent adamantyl.

Preferably, when $X^1$ and $X^2$ in the compound of formula IIIa independently represent congressyl, then $X^3$ and $X^4$ in the compound of formula IIIb independently represent congressyl, $X^5$ and $X^6$ in the compound of formula IIIc independently represent congressyl, and $X^7$ and $X^8$ in the compound of formula IIId independently represent congressyl.

Preferably, when $X^1$ and $X^2$ together with $Q^2$ to which they are attached in the compound of formula IIIa form a 2-phospha-adamantyl group, then $X^3$ and $X^4$ together with $Q^1$ in the compound of formula IIIb, $X^5$ and $X^6$ together with $Q^3$ in the compound of formula IIIc, and $X^7$ and $X^8$ together with $Q^4$ in the compound of formula IIId each independently form a 2-phospha-adamantyl group.

Preferably, when $X^1$ and $X^2$ together with $Q^2$ to which they are attached in the compound of formula IIIa forms a ring system of formula Ia, then $X^3$ and $X^4$ together with $Q^1$ in a compound of formula IIIb, $X^5$ and $X^6$ together with $Q^3$ in a compound of formula IIIc, and $X^7$ and $X^8$ together with $Q^4$ in a compound of formula IIId, form a ring system of formula Ib, Ic and Id, respectively.

Most preferably, the compounds of formula IIIa, IIIb, IIIc and IIId are identical.

Suitably, when preparing the 1,2,3,4-substituted derivative of the compound of formula I, preferably $LG_1$, $LG_2$ and $LG_3$ of the compound of formula IX do not represent hydroxyl, but each represents $NR^{23}R^{24}$ as defined herein.

Similarly, a compound of formula I wherein K represents $-A_3-Q^3(X^5)X^6$, D represents $-A_4-Q^4(X^7)X^8$, and E represents $-A_5-Q^5(X^9)X^{10}$ may be prepared from a compound of formula XI

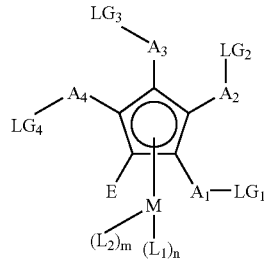

(XI)

wherein $A_1, A_2, A_3, LG_1, LG_2, LG_3, M, L_1, L_2$, n and m are as defined for a compound, of formula IX, $A_4$ is as defined for a compound of formula I, $LG_4$ represents a leaving group, and E represents hydrogen, by sequential ortho-lithiation and reaction with a compound of V(e)

$$A_5=LG_5 \quad (Ve)$$

wherein $A_5$ is as defined for a compound of formula I and $LG_5$ represents oxygen or $NR^{23}R^{24}$ as defined herein, followed by reaction of the resultant compound with a phosphine, arsine or stilbene derivative of formula IIIa, IIIb, IIIc, IIId as defined herein and formula IIIe $$HQ^5(X^9)X^{10} \quad (IIIe)$$

wherein $X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ form a 2-phospha-adamantyl group, or $X^9$ and $X^{10}$ together with $Q^5$ form a ring system of formula Ie, and $R^{37}$ to $R^{42}$, adamantyl, 2-phospha-adamantyl, $Q^5$ and the ring system of formula Ie are as defined for a compound of formula I.

Suitably, when preparing the 1,2,3,4,5-substituted derivative of formula I, preferably $LG_1$, $LG_2$, $LG_3$ and $LG_4$ of the compound of formula X do not represent hydroxyl, but each represents $NR^{23}R^{24}$ as defined herein.

Preferably, the compounds of formula IIIa, IIIb, IIIc, IIId and IIIe are identical.

Compounds of formula IIIa wherein $X^1$ and $X^2$ together with $Q^2$ to which they are attached form a 2-phospha-adamantyl group may be prepared by methods well known to those skilled in the art. Suitably, certain 2-phospha-adamantyl compounds are obtainable from Cytec Canada Inc of 901 Garner Road, Niagara Falls, Ontario, Canada L2E 6T4. Likewise corresponding 2-phospha-adamantyl compounds of formula IIIb, IIIc, IIId and IIIe may be obtained from the same supplier or prepared by analogous methods.

Compounds of formula IIIa where $X^1$ and $X^2$ represent adamantyl may be prepared by methods well known to those skilled in the art, for example by reacting adamantane (or substituted derivative thereof as defined herein) with phosphorous trichloride and aluminium chloride, followed by reduction of the intermediate $(adamantyl)_2$-P(O)Cl derivative. Likewise corresponding compounds of formula IIIb, IIIc, IIId and IIIe where $X^2$ to $X^{10}$ respectively represent adamantyl may be prepared by analogous methods.

Compounds of formula IIIa where $X^1$ and $X^2$ together with $Q^2$ to which they are attached form a ring system of formula Ia may be prepared by reacting a phosphine ($PH_3$) with a compound of formula XII

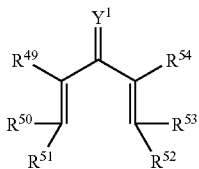

(XII)

where $Y^1$ and $R^{49}$ to $R^{55}$ are as defined for a compound of formula I. Corresponding compounds of formula IIIb, IIIc, IIId and IIIe may be synthesised by analogous methods.

Conveniently, a compound of formula I wherein K, D, E, M, $A_2$, $A_1$, $L_2$, $L_1$, $Q^1$, $Q^2$, m and n are as defined for a compound of formula I and $X^1$ and $X^2$ together with $Q^2$ to which they are attached form a ring system of formula Ia and $X^3$ and $X^4$ together with $Q^1$ to which they are attached form a ring system of formula Ib, may be formed by reacting a compound of formula XV

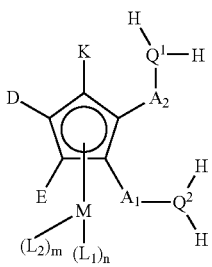

(XV)

wherein K, D, E, M, $A_2$, $A_1$, $L_2$, $L_1$, $Q^1$, $Q^2$, m and n are as defined for a compound of formula I, with a compound of formula XVIa and XVIb

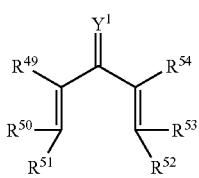

(XVIa)

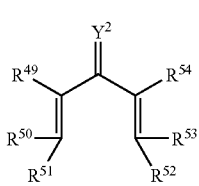

(XVIb)

wherein $Y^1$, $Y^2$, $R^{49}$ to $R^{55}$ are as defined for a compound of formula I.

Suitably, the reaction may be accomplished by heating the reactants at 120° C. for approximately 20 hours.

Thus according to a fifth aspect, the present invention provides a compound of formula XV as defined herein.

Similarly, a compound of formula I wherein D, E, M, $A_2$, $A_1$, $L_2$, $L_1$, $Q^1$, $Q^2$, m and n are as defined for a compound of formula I, $X^1$ and $X^2$ together with $Q^2$ to which they are attached form a ring system of formula Ia, $X^3$ and $X^4$ together with $Q^1$ to which they are attached form a ring system of formula Ib, and K represents $-A_3-Q^3(X^5)X^6$ wherein $X^5$ and $X^6$ together with $Q^3$ to which it is attached form a ring system of formula Ic and $A_3$ is as defined for a compound of formula I, may be formed by reacting a compound of formula XVII

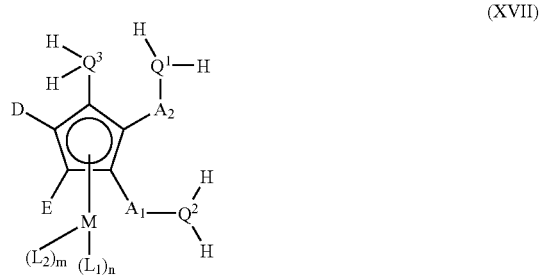

(XVII)

wherein D, E, M, $A_2$, $A_1$, M, $L_2$, $L_1$, $Q^1$, $Q^2$, $Q^3$, m and n are as defined for a compound of formula I, with a compound of formula XVIa, XVIb, XVIc

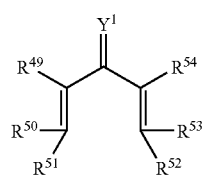

(XVIa)

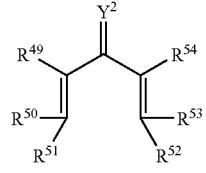

(XVIb)

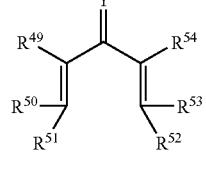

(XVIc)

wherein $Y^1$, $Y^2$, $Y^3$, $R^{49}$ to $R^{55}$ are as defined for a compound of formula I.

Preferably, $Y^1$ is the same as $Y^2$ and $Y^3$ in a compound of formula XVIa, XVIb and XVIc. Most preferably, the compounds of formula XVIa, XVIb and XVIc are identical.

Suitably, the compound of formula XV may be prepared from a compound of formula XVIII, where K, D, E, M, $L_2$, $L_1$, $A_1$, $A_2$, $Q^1$, $Q^2$, n and m are as defined for a compound of formula XV,

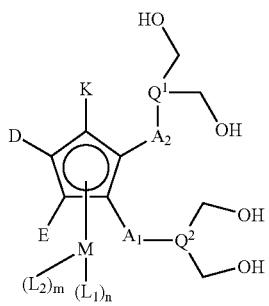

(XVIII)

by reduction with for example, sodium metabisufite.

Suitably the compound of formula XVIII may be prepared from a compound of formula XIX wherein K, D, E, M, $A_2$, $A_1$, $L_2$, $L_1$, m and n are as defined for a compound of formula XVIII

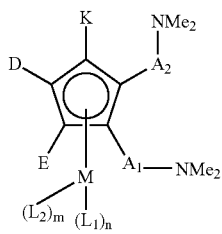

(XIX)

by reaction with an alkyl iodide, such as methyl iodide, to form the 1,2-bis-methyl iodide salt derivative of the compound of formula XIX followed by reaction with tris-hydroxymethyl phosphine/stilbene/arsine.

It will be appreciated by those skilled in the art that 1, 2, 3, 4 and 1, 2, 3, 4, 5 substituted compounds may be prepared by analogous methods.

The compounds of formula IIIa, IIIb, IIIc, IIId, IIIe, Va, Vb, Vc, Vd, Ve, VIII, XV, XVIa, XVIb, XVIc, XVII, XIX and derivatives thereof, when neither commercially available nor subsequently described, may be obtained using conventional synthetic procedures in accordance with standard text books on organic chemistry or literature precedent, from readily accessible starting materials using appropriate reagents and reaction conditions.

It will be appreciated by those skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps.

It will also be appreciated that various standard substituents or functional group interconversions and transformations within certain compounds of formula I will provide other compounds of formula I.

According to a sixth aspect, the present invention provides a process for the carbonylation of an ethylenically unsaturated compound comprising contacting an ethylenically unsaturated compound with carbon monoxide and a coreactant in the presence of a compound of the present invention.

Suitable coreactants include compounds comprising a nucleophilic moiety and a mobile hydrogen atom. Thus the compounds of the invention may catalyse hydroformylation, hydrocarboxylation, hydroesterification and hydroamidation reactions of an ethylenically unsaturated compound.

Preferred coreactants include molecular hydrogen, water, alcohols, primary or secondary amines or amides, such as diethylamine, N,N-dimethylethylene diamine, carboxylic acids for example acetic acid, propionic acid and pivalic acid, and aromatic alcohols.

Preferably, the coreactant has a hydroxyl functional group or is molecular hydrogen. The hydroxyl containing compounds may be branched or linear, and comprises an alkanol, particularly a $C_1$-$C_{30}$ alkanol, such as neopentyl alcohol, ethylhexyl alcohol, tert-amyl alcohol, including aryl-alkanols, which may be optionally substituted with one or more substitutents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, n-butanol, octanol, phenol and chlorocapryl alcohol. Although the monoalkanols are most preferred, polyalkanols, preferably, selected from di-octanols such as diols, triols, tetra-ols and sugars are also possible. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol.

The amount of alcohol is not critical. Generally, amounts are used in excess of the amount of ethylenically unsaturated compound to be carbonylated. Thus the alcohol may serve as the reaction solvent as well, although, if desired, separate solvents may also be used.

It will be appreciated that the end product of the reaction is determined at least in part by the source of coreactant compound used. If water is used as the hydroxyl group containing compound then the end product is the corresponding carboxylic acid, whereas use of an alkanol produces the corresponding ester.

Preferably, the ethylenically unsaturated compound includes from 2 to 20 carbon atoms. More preferably, the ethylenically unsaturated compound includes 2 to 14 carbon atoms.

Suitably, the ethylenically unsaturated compound may include more than one carbon-carbon double bond, wherein the double bonds are conjugated or non-conjugated.

Preferably, the ethylenically unsaturated compound has 1 to 3 carbon-carbon double bonds per molecule, particularly 1 to 2 carbon-carbon double bonds, especially only 1 carbon-carbon double bond per molecule.

Unless otherwise specified, the ethylenically unsaturated compound may, when there are a sufficient number of carbon atoms, be linear or branched, be cyclic, acyclic or part cyclic/acyclic, and/or be substituted or terminated by one or more substituents selected from lower alkyl, aryl, alkylaryl, Het, alkylHet, halo, $OR^{19}$, $OC(O)R^{20}$, $C(O)R^{21}$, $C(O)OR^{22}$, $NR^{23}R^{24}$, $C(O)NR^{25}R^{26}$, $NO_2$, $CN$, $SR^{27}$ wherein $R^{19}$ to $R^{27}$ each independently represent hydrogen or lower alkyl. Olefins thus substituted include styrene and alkyl esters of unsaturated carboxylic acids, such as methacrylate. Suitably, the ethylenically unsaturated compound may exhibit cis (E) and trans (Z) isomerism.

Examples of suitable ethylenically unsaturated compounds having 2 or more carbon atoms include ethene, propene, but-l-ene, but-2-ene, isobutene, pentenes, hexenes, octenes, dodecenes, 1,5-cyclooctadiene, cyclododecene, methyl pentenoate, pentene nitrile, 1,3 butadiene, 1,3 pentadiene, vinyl acetate and 1,3, hexadiene. Particularly preferred ethylenically unsaturated compounds include ethene, oct-1-ene, vinyl acetate and 1,3 butadiene, especially ethene.

The process according to the invention may be especially advantageous for the carbonylation of ethylenically unsaturated compounds which are internally unsaturated, such as but-2-ene, pent-2-ene nitrile, oct-2-ene, oct-3-ene, oct-4-ene or methyl pent-3-enoate. For these compounds side reactions typically occur more readily and linear products may be more difficult to obtain. Conveniently, the compounds of the invention may permit high regioselectivity towards a linear product following carbonylation of internally unsaturated ethylenic compounds.

Preferably, the carbonylation process is carried out at a temperature of from 0° C. to 250° C., more preferably 40° C. to 150° C., most preferably 70° C. to 120° C.

Suitably, the carbonylation process is typically carried out at a pressure of at least atmospheric pressure. Preferably, the carbonylation process is performed under a total pressure of greater than or equal to $1 \times 10^5$ $Nm^{-2}$, more preferably greater than or equal to $5 \times 10^5$ $Nm^{-2}$, most preferably greater than or equal to $10 \times 10^5$ $Nm^{-2}$. Preferably, the carbonylation process is performed under a total pressure of less than or equal to $100 \times 10^5$ $Nm^{-2}$, more preferably less than or equal to $65 \times 10^5$ $Nm^{-2}$, most preferably less than or equal to $50 \times 10^5$ $Nm^{-2}$.

Carbon monoxide partial pressures in the range of 1 to 65, particularly 5 to $50 \times 10^5$ $Nm^{-2}$, are preferred. In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compound to coreactant containing compound may vary between wide limits and suitably lies in the range of 1:0.1 to 1:10, preferably from 2:1 to 1:2.

The amount of the catalyst of the invention used in the carbonylation process of the ethylenically unsaturated compound is not critical. Good results may be obtained by using $10^{-7}$ to $10^{-3}$ moles, more preferably $10^{-6}$ to $10^{-2}$ moles, of Group VIIIB metal or a compound thereof (referred to as (a) herein) per mole of ethylenically unsaturated compound.

Preferably, as mentioned herein, the process is performed by the inclusion of a source of anions as defined herein in addition to the compounds of the invention. Suitably, a source of anions separate from the compounds of the invention may be added to the carbonylation process. Preferably, as mentioned herein, the compounds of the invention include a source of anions. Suitably, the mole ratio of anions to the moles of Group VIIIB metal in the compounds of the invention when used to carbonylate ethylenically unsaturated compounds lies between wide limits and suitably lies between 2:1 to 2000:1, preferably 10:1 to 200:1.

Suitably, the carbonylation of an ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane (diglyme), diethylether, tetrahydrofuran, diphenylether, diisopropylether and the dimethylether of di-ethylene-glycol; esters, such as for example methylacetate, dimethyladipate and butyrolactone; amides, such as for example dimethylacetamide and N-methylpyrrolidone; and sulfoxides and sulphones, such as for example dimethylsulphoxide, di-isopropylsulphone, sulfolane (tetrahydrothiophene-2,2-dioxide) 2-methylsulfolane and 2-methyl-4-ethylsulfolane.

Very suitable are aprotic solvents having a dielectric constant that is below a value of 50, more preferably in the range of 3 to 8, at 298.15 K and $1 \times 10^5$ $Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, 76$^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1 \times 10^5$ $Nm^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

If the coreactant compound is an alkanol, a further preferred aprotic solvent is the ester carbonylation product of the ethylenically unsaturated compound, carbon monoxide and the alkanol.

The process may advantageously be carried out in an excess of aprotic solvent, i.e. at a ratio (v/v) of aprotic solvent to coreactant containing compound of at least 1:1. Preferably, this ratio ranges from 1:1 to 10:1 and more preferably from 1:1 to 5:1. Most preferably the ratio (v/v) ranges from 1.5:1 to 3:1.

The catalyst compounds of the present invention may act as a "heterogeneous" catalyst or a "homogeneous" catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a seventh aspect, the present invention provides a catalyst system comprising a support, preferably an insoluble support, and a compound of the invention as defined herein. Conveniently, the use of an insoluble support permits easy separation of the catalyst, for example by filtration, from the reaction medium.

Preferably, the support comprises a polymer such as a polyolefin, polystyrene and polystyrene/divinylbenezene copolymer; a silicon derivative such as a functionalised silica, a silicone or a silicone rubber; or other porous particulate material such as for example inorganic oxides and inorganic chlorides such as alumina and montmorillomite.

Preferably the support material is porous silica which has a surface area in the range of from 10 to 700 $m^2/g$, a total pore volume in the range of: from 0.1 to 4.0 cc/g and an average particle size in the range of from 10 to 500 μm. More preferably, the surface area is in the range of from 50 to 500 $m^2/g$, the pore volume is in the range of from 0.5 to 2.5 cc/g and the average particle size is in the range of from 20 to 200 μm.

Most desirably the surface area is in the range of from 100 to 400 m²/g, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compound of the invention by techniques well known to those skilled in the art. Alternatively, the compound of the invention is fixed to the surface of insoluble support, optionally via a covalent bond, and optionally includes a bifunctional spacer molecule to space the compound from the insoluble support.

The compounds of the invention may be fixed to the surface of the insoluble support by promoting reaction of a functional group present in the compound of formula I, for example a substituent of the ligand $L_1$ or a substituent K, D and E of the cyclopentadienyl moiety, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the present invention to the support depend upon the nature of the substituents(s) of the compound and the groups of the support. For example, reagents such as carbodiimides, 1,1'-carbonyldiimidazole, and processes such as the use of mixed anhydrides, reductive amination may be employed.

According to an eighth aspect, the present invention provides the use of a compound of the invention or a compound of the invention attached to a support as a catalyst.

It will be appreciated that any of the features set forth in the first aspect of the invention may be regarded as preferred features of the second, third, fourth, fifth, sixth, seventh and eighth aspect of the present invention and vice versa.

The invention will now be described by way of the following non-limiting examples.

EXAMPLE 1

Preparation of
1,2-bis-(dimethylaminomethyl)ferrocene n-Butyllithium (Aldrich, 2.5 molar in hexane, 24 ml, 54 mmol) is added to a solution of (dimethylaminomethyl)ferrocene (Aldrich, 13.13 g, 10.69 ml, 48.97 mmol) in diethyl ether (80 ml) under nitrogen at a temperature of 25° C. and the reaction mixture stirred for 4 hours. The resulting red solution is then cooled to approximately −70° C. in a dry ice/acetone bath and Eschenmosers salt (ICH$_2$NMe$_2$)(Aldrich, 10 g, 54 mmol) is added. The reaction is allowed to warm to room temperature and stirred overnight.

The resultant solution is quenched with excess aqueous sodium hydroxide and the resulting product extracted with diethyl ether (3×80 ml) dried over anhydrous magnesium sulfate, filtered over celite, and volatiles removed in vacuo to yield the crude title compound as a light orange crystalline solid. The crude product is recrystallised from light petrol with cooling to −17° C. and the recrystallised product washed with cold petrol to yield the title compound as a light orange solid (13.2 g, 74%). The compound can be further purified by sublimation to give 8.5 g (52%) of the title compound (mpt 74° C.).

$^1$H NMR (250 MHz; CDCl$_3$): δ4.23(brd, 2H); 4.11-4.10(t, 1H); 4.04(s, 5H); 3.43, 3.38, 3.23, 3.18 (AB quartet, 2H); 2.22(s, 6H).

$^{13}$C NMR (63 MHz; CDCl$_3$): δ83.81; 70.40; 69.25; 66.84; 57.35; 45.23.

Elemental analysis: Found: C, 63.7%; H, 8.9%; N, 9.5%
Calculated: C, 64.0%; H, 8.1%; N, 9.4%

EXAMPLE 2

Preparation of
1,2-bis-(ditertbutylphosphinomethyl)ferrocene

Di-tertbutylphosphine (Aldrich, 0.616 ml, 3.33 mmol) was added to a solution of 1,2-bis(dimethylaminomethyl)ferrocene (Example 1, 0.5 g, 1.66 mmol) in anhydrous acetic acid (100 ml) under nitrogen and the resulting mixture is stirred at 80° C. for 72 hours. The anhydrous acetic acid is removed in vacuo at approximately 70° C. to yield the crude title product as an orange/yellow solid. The crude product is recrystallised from ethanol with cooling to −17° C., filtered and the filtrate washed with cold ethanol to yield the title compound as a pale yellow solid (0.365 g, 44%, 84° C.).

$^1$H NMR (250 MHz; CDCl$_3$): δ4.4 (2H, d, J=2 Hz); 3.95 (5H, s); 3.75 (1H, t, 2 Hz); 2.8 (2H, dd, 12 Hz, 2 Hz); 2.6 (2H, dd, 12 Hz, 2 Hz); 1.1 (36H, m).

$^{13}$C NMR (63 MHz; CDCl$_3$): δ86.73 (d, 5.46 Hz); 70.08 (d, 4.41 Hz); 69.4665(s); 63.75(s); 31.80 (d, 2 Hz); 31.45 (d, 1.98 Hz); 29.89 (d, 1.88 Hz).

$^{31}$P NMR (101 MHz; CDCl$_3$): δ15.00 ppm.

Elemental analysis: Found: C, 66.79%; H, 9.57%
Calculated: C, 66.93%; H, 9.63%

EXAMPLE 3

Preparation of
1-hydroxymethyl-2-dimethylaminomethyl ferrocene n-Butyl lithium (Aldrich, 1.6 molar in diethyl ether, 5.14 ml, 8.24 mmol) is added to a solution of 1-dimethylaminomethyl ferrocene (Aldrich, 1.0 g, 4.12 mmol) in diethyl ether (20 mL) under argon. The reaction is stirred for 3 hours and developes a reddish colour. The solution is then cooled in a dry ice/acetone bath, calcined paraformaldehyde (0.247 g, 2 times excess) added and the resultant mixture stirred overnight at room temperature. The reaction is then quenched with water, extracted with diethyl ether, dried over MgSO$_4$, and filtered over celite. The solvent is removed in vacuo to yield crude title compound. The crude product is applied to a neutral alumina column, which is eluted with petrol/diethyl ether (9:1 ratio) to remove the starting material, 1-dimethylaminomethyl ferrocene. The column is then eluted with substantially pure ethyl acetate to elute the title compound. The ethyl acetate is removed in vacuo, to yield the title compound as an orange oil/crystalline mass.

$^1$H NMR (250 MHz; CDCl$_3$) δ2.131 (s, 6 H), δ2.735. (d, 1 H, 12.512 Hz), δ3.853 (d, 1 H, 12.512 Hz), δ3.984 (dd, 1 H, 2.156 Hz), δ4.035 (s, 5 H), δ4.060 (dd, 1 H, 2.136 Hz) δ4.071 (d, 1 H, 12.207 Hz), δ4.154 (m, 1 H), δ4.73 (d, 1 H, 12.207 Hz).

$^{13}$C NMR (61 MHz; CDCl$_3$) δ7.688, δ84.519, δ70.615, δ68.871, δ68.447, δ65.369, δ60.077, δ58.318, δ44.414

COSY 2D $^1$H NMR

Partly obscured doublet at 4.071 ppm and its coupling to the doublet at 4.73 ppm confirmed.

Infrared spectra (CHCl$_3$)(c.a. 0.06 g/0.8 mL) 2953.8 cm$^{-1}$, 2860.6 cm$^{-1}$, 2826.0 cm$^{-1}$, 2783.4 cm$^{-1}$, 1104.9 cm$^{-1}$

EXAMPLE 4

Preparation of 1,2-bis-(ditertbutylphosphinomethyl)ferrocene

Di-tertbutylphosphine (Aldrich, 0.54 ml, 2.93 mmol) is added to a solution of 1-hydroxymethyl-2-dimethylaminomethyl ferrocene (Example 3, 0.2 g, 0.753 mmol) in anhydrous acetic acid (15 ml) and acetic anhydride (0.753 mmol) under argon and the resulting mixture is stirred at 80° C. for 72 hours. The anhydrous acetic acid is removed in vacuo at approximately 70° C. to yield the crude title product as an orange/yellow solid. The crude product is recrystallised from ethanol with cooling to −17° C., filtered and the filtrate washed with cold ethanol to yield the title compound as an orange solid (0.23 g)

$^1$H NMR (250 MHz; CDCl$_3$) δ4.351 (d, 2 H, 2 Hz), δ4.022 (s, 5 H), δ3.827 (t, 1 H, 2 Hz), δ2.858 (ddd, 2 H, J$_{HH}$ 15.869 Hz, J$_{HP1}$3.320 Hz, J$_{HP2}$ 1.831 Hz), δ2.679 (dd, 2 H, J$_{HH}$ 15.869 Hz, J$_{HP}$ 2.441 Hz), δ1.166 (d, 18 H, 12.817 Hz), δ1.123 (d, 18 H, 12.512 Hz)

FTIR (Chloroform, NaCl plates)

1104.1 cm$^{-1}$, 2863 cm$^{-1}$, 2896.0 cm$^{-1}$, 2940.0 cm$^{-1}$, 2951.8 cm$^{-1}$ $^{31}$P NMR (101 MHz; CDCl$_3$): δ15.00 ppm.

Elemental analysis: Found: C, 66.5%; H, 9.6%
Calculated: C, 66.9%; H, 9.6%

EXAMPLE 5

Preparation of 1-hydroxymethyl-2,3-bis-(dimethylaminomethyl)ferrocene

To a stirred solution of 1,2-bis-(dimethylaminomethyl) ferrocene (Example 1, 0.70 g, 2.32 mmol) in diethyl ether (15 cm$^3$) under argon is added 1.2 equivalents n-butyl lithium (Aldrich, 1.75 mL, 1.6M in diethyl ether) and the mixture stirred for three hours to yield a red solution. The reaction mixture is cooled in a dry ice/acetone bath, calcined paraformaldehyde added in 2:1 excess, and the resultant mixture stirred at room temperature overnight. The mixture is quenched with water and extracted with diethyl ether. The ethereal extracts are dried over MgSO$_4$, filtered over celite and the solvent removed in vacuo, to yield the title compound (0.7 g, 2.12 mmol, 91%) as an orange oil, which partially crystallized on cooling.

$^1$H NMR (250 MHz; CDCl$_3$) δ 2.133 (s, 6 H), δ 2.171 (s, 6 H), δ 2.910 (d, 1 H, 12.817 Hz), δ 2.998 (d, 1 H, 12.512 Hz), δ 3.425 (d, 1 H, 12.817 Hz), δ 3.812 (d, 1 H, 12.512 Hz), δ 3.962 (s, 5 H), δ 3.99 (d, 1 H, 12.207 Hz) (partly obscured by large cp-ring peak at δ 3.962), δ 4.068 (d, 1 H, δ82.136 Hz), δ 4.125)d, 1 H, δ 2.136 Hz), δ 4.747 (d, 1 H, 12.207 Hz)

$^{13}$C NMR (60 MHz; CDCl$_3$) δ44.529, δ45.244, δ55.798, δ57.906, δ60.271, δ67.944, δ68.277, δ69.612, δ84.850, δ888.322

Infrared spectra (CDCl$_3$/thin film NaCl plates)

3380.6 cm$^{-1}$ (br), 2955.7 cm$^{-1}$ (m), 2862.6 cm$^{-1}$, 2825.9 cm$^{-1}$, (m), 2774.3 cm$^{-3}$ (m), 1353.5 cm$^{-1}$ (m), 1104.9 cm$^{-1}$ (m), 1038.9 cm$^{-1}$ (m), 1006.8 cm$^{-1}$ (s)

Elemental analysis: Found: C, 62.3%; H, 7.8%; N, 8.8%
Calculated: C, 61.8%; H, 7.9%; N, 8.5%

EXAMPLE 6

Preparation of 1,2,3-tris-(ditertbutylphosphinomethyl)ferrocene

Di-tert-butylphosphine (Aldrich, 2.60 mL, 13.98 mmol) and acetic anhydride (0.24 mL, 2.33 mmol) is added to a solution of 1-hydroxymethyl-2,3-bis-(dimethylaminomethyl)ferrocene (Example 5, 0.70 g, 2.12 mmol) in acetic acid (freshly distilled from acetic anhydride 25 cm$^3$), under argon. The solution is then stirred at 80° C. for 7 days, during which time the solution becomes a dark orange colour. The solvent is then removed in vacuo and recrystallisation effected from refluxing ethanol together with cooling to −17° C. overnight to yield the title compound (0.43 g, 0.7 mmol, 31%) as a yellow/orange powder.

$^1$H NMR (250 MHz, CDCl$_3$) δ 1.12 (dd-pseudo triplet, 36 H, 12.1 Hz), δ1.26 (d, 18H, 10.7 Hz), δ2.68 (d, 2 H, 17.7 Hz), δ2.95 (s, 2 H), δ3.07, (m, 2 H), δ4.01 (s, 5 H) δ 4.33 (s, 2 H)

Infrared spectra (CHCl$_3$/thin film NaCl plates)

1365.5 cm$^{-1}$, 1470.3 cm$^{-1}$, 2357.1 cm$^{-1}$, 2862.8 cm$^{-1}$, 2896.7 cm$^{-1}$, 2939.1 cm$^{-1}$

EXAMPLE 7

Preparation of 1,2-bis-(dicyclohexylphosphinomethyl)ferrocene

The title compound was prepared in accordance with the procedure of Example 2 employing dicyclohexylphosphine (Strem of 48 High Street Orwell, Royston, United Kingdom SG8 5QW, 659 mg, 3.33 mmol), 1,2-bis(dimethylaminomethyl)ferrocene (0.5 g, 1.66 mmol) and anhydrous acetic acid (100 ml). Yield 0.421 g.

EXAMPLE 8

Preparation of 1,2-bis-(di-iso-butylphosphinomethyl)ferrocene

The title compound was prepared in accordance with the procedure of Example 2 employing di-iso-butylphosphine (Strem 486 mg, 3.33 mmol), 1,2-bis(dimethylaminomethyl) ferrocene (0.5 g, 1.66 mmol) and anhydrous acetic acid (100 ml). Yield 0.372 g.

EXAMPLE 9

Preparation of 1,2-bis-(dicyclopentylphosphinomethyl)ferrocene

The title compound was prepared in accordance with the procedure of Example 2 employing dicyclopentylphosphine (Strem 566 mg, 3.33 mmol), 1,2-bis(dimethylaminomethyl) ferrocene (0.5 g, 1.66 mmol) and anhydrous acetic acid (100 ml). Yield 0.432 g.

EXAMPLE 10

Preparation of 1,2-bis-(diethylphosphinomethyl) ferrocene

The title compound was prepared in accordance with the procedure of Example 2 employing diethylphosphine (Strem 299 mg, 3.33 mmol), 1,2-bis(dimethylaminomethyl)ferrocene (0.5 g, 1.66 mmol) and anhydrous acetic acid (100 ml). Yield 0.254 g.

EXAMPLE 11

Preparation of 1,2-bis(di-isopropylphosphinomethyl)ferrocene

The title compound was prepared in accordance with the procedure of Example 2 employing di-iso-propylphosphine (Digital Speciality Chemicals 392 mg, 3.33 mmol), 1,2-bis(dimethylaminomethyl)ferrocene (0.5 g, 1.66 mmol) and anhydrous acetic acid (100 ml). Yield 0.262 g.

EXAMPLE 12

Preparation of 1,2-bis-(dimethylphosphinomethyl)ferrocene

The title compound was prepared in accordance with the procedure of Example 2 employing dimethylphosphine (Digital Speciality Chemicals, 206 mg, 3.33 mmol), 1,2-bis(dimethylaminomethyl)ferrocene (0.5 g, 1.66 mmol) and anhydrous acetic acid (100 ml). Yield 0.285 g.

EXAMPLE 13

Preparation of 1,2-bis-(diadamantylphosphinomethyl)ferrocene bis-methanesulphonate Di-adamantylphosphine (prepared according to J. R. Goerlich, R. Schmutzler; Phosphorus Sulphur and Silicon; 1995, 102, 211-215, 20.0 g, 0.066 mol) was added to a solution of 1,2-bis(dimethylaminomethyl)ferrocene (Example 1, 10 g, 0.033 mol) in anhydrous acetic acid (100 ml) under nitrogen and the resulting mixture is stirred at 80° C. for 72 hours. The orange yellow precipitate which forms is filtered and dried in vacuo at approximately 70° C. to yield the title compound as an orange/yellow solid. The title compound is insoluble in a range of organic solvents and it is therefore purified by conversion to the bis-methanesulphonate salt by addition of excess methanesulphonic acid to a methanol slurry of the crude product. This resulted in complete dissolution of the product salt which was then isolated by removal of the methanol in vacuo followed by washing with ether and drying to give the title compound as a pale yellow solid (14.0 g, 54%).
$^1$H NMR (250 MHz; CD$_3$CN): δ4.57 (2H, d, J=2 Hz); 4.35 (5H, s); 4.27 (1H, t, 2 Hz); 3.34 (4H, br); 2.6 (6H, br,); 2.35-2.18 (18H br); 2.16-2.0 (18H, br); 1.92-1.72 (24H, br).
$^{31}$P NMR (101 MHz; CD$_3$CN): δ26.58 ppm.
Elemental analysis: Found: C, 64.15%; H, 7.88% Calculated: C, 64.29%; H, 7.94%

EXAMPLE 14

Preparation of 1,2bis(di-1-adamantylphosphinomethyl)ferrocene-bis-methane sulphonate The preparation of this ligand was carried out as follows:

14.1 Preparation of (1-Ad)$_2$P(O)Cl
Phosphorous trichloride (83 cm$^3$, 0.98 mol) was added rapidly via cannula to a combination of aluminium chloride (25.0 g, 0.19 mol) and adamantane (27.2 g, 0.20 mol) affording a tan suspension. The reaction was heated to reflux. After 10 minutes, a yellow-orange suspension was formed. The reaction was refluxed for a total of 6 hours. The excess PCl$_3$ was removed by distillation at atmospheric pressure (BP 75° C.). On cooling to ambient temperature, an orange solid was formed. Chloroform (250 cm$^3$) was added yielding an orange suspension, which was cooled to 0° C. Water (150 cm$^3$) was added slowly: initially the suspension viscosity increased, but on full addition of water the viscosity lessened. From this point the reaction was no longer kept under an atmosphere of Ar. The suspension was Buchner filtered to remove the yellow-orange solid impurity. The filtrate consisted of a two phase system. The lower phase was separated using a separating funnel, dried over MgSO$_4$ and Buchner filtered. The volatiles were removed via rotary evaporation, drying finally in-vacuo, affording an off-white powder. Yield 35.0 g, 99%.
$^{31}$P NMR:=85 ppm, 99% pure. FW=352.85.

14.2 Preparation of (1-Ad)$_2$PH
LiAlH$_4$ (2.54 g, 67.0 mmol) was added over 90 minutes to a chilled (−10° C.) solution of (1-Ad$_2$P(O)Cl (10.00 g, 28.3 mmol) in THF (120 cm$^3$). The reaction was allowed to warm to ambient temperature then stirred for 20 hours. The grey suspension was cooled to −10° C. HCl (aq. 5 cm$^3$ c. HCl in 50 cm$^3$ degassed water) was added slowly via syringe (initially very slowly due to exotherm of reaction), yielding a two phase system, with some solid material in the lower phase. Further HCl (~5 cm$^3$ c. HCl) was added to improve the separation of the layers. The upper phase was removed via flat ended cannula, dried over MgSO$_4$ and filtered via cannula. The volatiles were removed in-vacuo affording the product as a white powder, isolated in the glovebox. Yield 6.00 g, 70%.
$^{31}$P NMR:=17 ppm, 100% pure. FW=302.44.

14.3 Preparation of 1,2-bis(di-1-adamantylphosphinomethyl)ferrocene-bis-methanesulphonate
The title compound was prepared in accordance with the procedure exemplified in Example 13.

EXAMPLE 15

Preparation of 1,2-bis(di-1-(3,5-dimethyladamantyl)phosphinomethyl) ferrocene-bis-methanesulphonate 15.1 Di-1-(3,5-dimethyladamantyl) phosphinic chloride was prepared in accordance with the method of Example 14.1 except using 1,3 dimethyladamantane 21.7 g (0.132 mol) instead of adamantane, and AlCl$_3$ (18.5 g, 0.14 mol). Yield 23.5 g FW: 409.08. $^{31}$P NMR: δ: 87 ppm (s).

15.2 Di-1-(3,5-dimethyladamantyl) phosphine was prepared as Example 14.2 above except using 25.0 g Di-1-(3,5-dimethyladamantyl)phosphinic chloride instead of di-l-adamantyl phosphinic chloride. Yield 15.7 g, FW: 358.58. $^{31}$P NMR: δ: 15.7 ppm (s).

15.3 1,2-bis-(di-1-(3,5-dimethyladamantylphosphinomethyl) ferrocene-bis-methanesulphonate
The title compound was prepared in accordance with the procedure exemplified in Example 13 except using di-1-2(3,5-dimethyl-adamantyl)phosphine (23.69 g, 0.066 mol) instead of di-adamantylphosphine. Yield 15 g.

EXAMPLE 16

Preparation of 1,2-bis(di-1-(4-tert-butyl-adamantyl)phosphinomethyl)ferrocene-bis-methanesulphonate 16.1 Di-1-(4-tert-butyladamantyl) phosphinic chloride was prepared as per Di-1-adamantyl phosphinic chloride of Example 14.1 except using 4-tert-butyladamantane 25.37 g (0.132 mol) instead of adamantine, and AlCl$_3$ (18.5 g, 0.14 mol). Yield 22.6 g FW: 464.98. $^{31}$P NMR: δ: 87 ppm (s).

16.2 Di-1-(4-tert-butyladamantyl) phosphine was prepared as per Di-1-adamantyl phosphine of Example 14.2 except using 13.5 g Di-1-(4-tert-butyladamantyl) phosphinic chloride instead of di-1-adamantyl phosphinic chloride. Yield 9.4 g, FW: 414.48. $^{31}$P NMR: δ: 18.62 ppm (s).

16.3 1,2-bis(di-1-(4-tert-butyl-adamantyl)phosphinomethyl)ferrocene-bis-methanesulphonate The title compound was prepared in accordance with the procedure exemplified in Example 13 except using di-1-(4-tert-butyladamantyl)phosphine (27.39 g, 0.066 mol) instead of di-adamantyl phosphine. Yield 14.52 g.

EXAMPLE 17

Preparation of 1,2-bis-(1-adamantyl tert-butyl-phosphinomethyl)ferrocene-bis-methanesulphonate 17.1 1-adamantylphosphonic acid dichloride This compound was synthesised according to the method of Olah et al (J. Org. Chem. 1990, 55, 1224-1227).

17.2 1-adamantyl phosphine

LiAlH$_4$ (3.5 g, 74 mmol) was added over 2 hours to a cooled solution (0° C.) of 1-adamantylphosphonic acid dichloride (15 g, 59 mmol) in THF (250 cm$^3$). The reaction was then allowed to warm to ambient temperature and was stirred for 20 hours. The grey suspension was then cooled (0° C.) and HCl (75 cm$^3$, 1M) was slowly added via syringe, to afford a two phase system with some solid present in the lower phase. Concentrated HCl (8 cm$^3$, 11M) was then added to improve the separation of the two layers. The (upper) THF phase was removed via cannula and dried over magnesium sulphate. After filtration via cannula, the volatiles were removed in-vacuo to afford the product.

17.3 1-adamantyl tert-butyl phosphine nBuLi (20 cm$^3$, 32 mmol 1.6M soln) was added over 1 hour to a cooled solution of 1-adamantyl phosphine (5.0 g, 30 mmol) in THF (100 cm$^3$). The solution was allowed to warm to room temperature and stirred for a further 2 hours. The solution was recooled to 0° C. and tert-butylchloride (2.78 g, 30 mmol) was added and stirring continued for a further 16 hours at room temperature. The reaction mixture was quenched with water and the aqueous phase extracted with dichloromethane (2×50 ml). The organic phase was dried over sodium sulphate and evaporated in-vacuo to yield the title compound.

17.4 1,2-bis-(-1-adamantyl tert-butyl-phosphinomethyl)ferrocene-bis-methanesulphonate The title compound was prepared in accordance with the procedure exemplified in Example 13 except using 1-adamantyl tert-butyl phosphine (14.78 g, 0.066 mol) instead of di-adamantyl phosphine. Yield 9.80 g.

EXAMPLE 18

Preparation of 1,2-bis-(di-1-diamantylphosphinomethyl)ferrocene-bis-methanesulphonate 18.1 Diamantane This was synthesised according to the method of Tamara et al. Organic Syntheses, CV 6, 378.

18.2 Di-1-(diamantane) phosphinic chloride

Prepared as per Di-1-adamantyl phosphinic chloride of Example 14.1 except using diamantane 20.0 g (0.106 mol) and AlCl$_3$ (16.0 g, 0.12 mol). Yield 25.5 g FW: 456.5. $^{31}$P NMR: δ: 87 ppm (s).

18.3 Di-1-(diamantane) phosphine

Prepared as per Di-1-adamantyl phosphine of Example 14.2 except using 25.0 g Di-1-(diamantane) phosphinic chloride. Yield 14.0 g FW: 406. $^{31}$P NMR: δ: 16.5 ppm (s).

18.4 1,2-bis-(di-1-diamantylphosphinomethyl)ferrocene-bis-methanesulphonate

The title compound was prepared in accordance with the procedure exemplified in Example 13 except using di-1-diamantane phosphine (26.79 g, 0.066 mol) instead of di-adamantyl phosphine. Yield 12.5 g.

EXAMPLE 19

Preparation of 1,2-bis-(di-(1,3,5,7-tetramethyl-6,9,10-trioxa-2-phoshpa-adamantylmethyl))ferrocene 1,3,5,7-tetramethyl-2,4,8-trioxa-6-phospha-adamantane (obtained from Cytec, 14.0 g, 0.066 mol) was added to a solution of 1,2-bis(dimethylaminomethyl)ferrocene (Example 1, 10 g, 0.033 mol) in anhydrous acetic acid (100 ml) under nitrogen and the resulting mixture is stirred at 80° C. for 72 hours. The anhydrous acetic acid is removed in vacuo at approximately 70° C. to yield the crude title product as an orange/yellow solid. This is washed with hot methanol to give the product as a mixture of isomers as an orange solid. (12.0 g, 58%).

$^1$H NMR (250 MHz; CDCl$_3$): δ4.25-3.95 (8H, br, m); 3.46 (4H, br); 1.57-2.0 (8H, br, m); 1.43-1.23 (24H, br m).

$^{31}$P NMR (101 MHz; CDCl$_3$): 5-27.41 (br), −29.01 (s), −33.9 (br) ppm.

Elemental analysis: Found: C, 57.80%; H, 7.35% Calculated: C, 57.87%; H, 7.40%

EXAMPLE 20

Preparation of 1,2-bis-(dimethylaminomethyl)ferrocence-bis methyl iodide

Methyl iodide (23.28 g, 0.164 mol) is added to a solution of 1,2-bis-(dimethylaminomethyl)ferrocence (Example 1, 20 g, 0.082 mol) in degassed methanol (100 ml), and the mixture stirred at room temperature under a nitrogen atmosphere for 24 hours. The resulting precipitate is removed by filtration, washed with ether and dried to yield the title compound (43.0 g).

Elemental analysis: Found: C, 36.8%; H, 5.1%; N, 4.8%
Calculated: C, 37.0%; H, 5.2%; N, 4.8%

$^{13}$C NMR (D$_2$O): δ53.27, δ53.21, δ53.15, δ64.68, δ71.77, δ73.24, δ74.13, δ874.95

EXAMPLE 21

Preparation of 1,2-bis(dihydroxymethylphosphinomethyl)ferrocene

Potassium hydroxide (8.52 g, 0.152 mol) is added to a solution of tetrakis(hydroxymethyl) phosphonium chloride (Aldrich, 38.54 g of 80% w/w aqueous solution, 0.162 mol) in degassed methanol (40 ml), and stirred at room temperature under a nitrogen atmosphere for 1 hour. The resultant mixture is added dropwise to a degassed solution of 1,2-bis-(dimethylaminomethyl)ferrocene-bis-methyl iodide (Example 20, 19.98 g, 52.2 mmol) in methanol (40 ml) under nitrogen at room temperature with stirring. The resultant mixture is refluxed under nitrogen for 20 hours, and the solvent removed in vacuo to form a red precipitate. Water (30 ml), diethyl ether (85 ml) and triethylamine (35 ml) is added to the precipitate and the solution stirred at room temperature for 1 hour. The aqueous layer is removed and re-extracted with diethyl ether (2×30 ml). The combined ethereal extracts are washed with water (3×20 ml) dried over sodium sulphate and filtered. The ether is removed in vacuo to yield the crude title compound (14.33 g, 94% yield) as a microcrystalline orange solid. The crude product is recrystallised from a warm dicholormethane/methanol solution with the addition of light petroleum and cooling to yield the title compound (10.69 g, 70% yield) as yello-orange crystals.

Elemental analysis: Found: C, 48.44%; H, 4.12%; N, 0.0%
Calculated: C, 48.24%; H, 4.02%; N, 0.0%

$^1$H NMR: $\delta 1.75$ (s, br), $\delta 2.70$ (dd, 2 H, $J^2_{HH}$ 14.2 Hz, $J^2_{HP}$ 6.6 Hz), $\delta 2.85$ (dd, 2 H, $J^2_{HH}$ 14.2 Hz, $J^2_{HP}$ 7.9 Hz), $\delta 3.71$ (t, 1 H, $J_{HH}$ 2.44 Hz), $\delta 3.58$ (s, 5 H), $\delta 3.98$ (d, 2 H, $J_{HH}$ 2.40 Hz), 4.06 (m, 8 H).

$^1$H{$^{31}$P} NMR: $\delta 1.75$ (s, br), $\delta 2.70$ (d, 14.3 Hz), $\delta 2.85$ (d, 14.3 Hz), $\delta 4.04$ (m, 1 H), $\delta 4.06$ (s, 8 H), $\delta 4.08$ (s, 5H), $\delta 4.1$ (m, 2 H)

$^{13}$C NMR: $\delta 23.7$ (d, $J^1_{PC}$ 15.6 Hz), $\delta 63.0$ (d, $J^1_{PC}$ 15.6 Hz), $\delta 66.0$ (s), $\delta 67.2$ (d, $J^3_{PC}$ 9.2 Hz), $\delta 69.6$ (s), $\delta 82.6$ (d, $J^2_{PC}$ 14.7 Hz)

$^{31}$P NMR: $\delta$ -14.7

Infrared spectra (CHCl$_3$/thin film NaCl plates)
3337.8 cm$^{-1}$(st, br), further peaks 1104 cm$^{-1}$ 2929.0 cm$^{-1}$, 3603.7 cm$^{-1}$, 3683.7 cm$^{-1}$.

EXAMPLE 22

Preparation of 1,2-bis(diphosphinomethyl)ferrocene 1,2-bis(dihydroxymethylphosphinomethyl)ferrocene (Example 21, 5.45 g, 13.70 mmol) and sodium metabisulfite (5.21 g, 27.4 mmol) is added to a two-phase solvent system consisting of distilled water (60 ml) and light petroleum (60 ml). The mixture is refluxed for 3 hours in air. The resultant mixture is cooled stirred and the aqueous layer removed. The organic layer is washed with distilled water and the organic solvent removed in vacuo to yield the title compound (2.66 g, 70% yield) as an orange crystalline solid.

Elemental analysis: Found: C, 51.65%; H, 5.75%
Calculated: C, 51.80%, H, 5.76%

$^1$H NMR (250 MHz; CDCl$_3$): $\delta$ 2.7-2.8 (m, 4H), $\delta$ 3.17 (m, 2H), $\delta$ 3.18 (m, 2H), $\delta$ 4.04 (t, 1H, J=2.54 Hz), $\delta$ 4.09 (d, 5H, $J_{HP}$ 0.4 Hz), $\delta$ 4.13 (d, 2H, J=2.54 Hz)

$^{31}$P NMR (101 MHz; CDCl$_3$): $\delta$ 130.0 (t, $J_{HP}$ 193.0 Hz)

$^{13}$C NMR (60 MHz; CDCl$_3$): $\delta$ 12.9, $\delta$ 65.6, $\delta$ 67.3, $\delta$ 69.4, $\delta$ 86.9

$^{13}$C DEPT NMR (CDCl$_3$): $\delta$ 12.9 (CH$^2$), $\delta$ 65.6 (CH), $\delta$ 67.3 (CH), $\delta$ 69.40 (5×CH)

FTIR (Chloroform, NaCl plates): 2298.5 cm$^{-1}$ (strong)
Mass spectrum: Found m/z: 278.0088; Calculated m/z 278.0077

EXAMPLE 23

Preparation of 1,2-bis-α,α-(P-(2,2,6,6,-tetramethylphosphinan-4-one))dimethylferrocene 2,6-Dimethyl-2,5-heptadiene-4-one (14.6 g, 0.106 mol) is added to 1,2-bis-(diphosphinomethyl)ferrocene (Example 22, 14.7 g, 0.053 mol) and the mixture heated to 120° C. under nitrogen for 20 hours. The reaction mixture is cooled, the crude title compound removed by filtration, washed with pentene (20 ml) and dried in vacuo to yield the title compound as a yellow-orange solid (24.9 g, 85% yield). The title compound was characterised by $^{31}$P NMR and mass spectrum.

$^1$H NMR (250 MHz; CDCl$_3$): d 4.32 (1H, br); 4.08 (5H, br); 4.02 (1H, br); 3.94 (1H br); 2.84 (4H, br); 1.8-2.5 (8H, br); 1.05-1.4 (24H, br,).

$^1$P NMR (101 MHz; CDCl$_3$): d 4.15 ppm.

Elemental analysis: Found: C, 64.26%; H, 7.88% Calculated: C, 65.03%; H, 7.94%

EXAMPLE 24

Preparation of Methyl Propanoate from Ethylene, Carbon Monoxide and Methanol Catalysed by a Compound of the Present Invention A mechanically stirred autoclave (Hastelloy) of 2 litre capacity was evacuated of air and then charged with a solution of tri(dibenzylideneacetone)dipalladium (1.44×10$^{-5}$ moles), 1,2-bis-(di-tertbutylphosphinomethyl)ferrocene of Example 2, (7.61×10$^{-5}$ moles) and methane sulfonic acid (2.25×10$^{-3}$ moles) in 300 ml of methyl propanoate/methanol (70 wt % methyl propanoate). The autoclave was heated to 100° C. and when at that temperature, ethylene (8×10$^5$ Nm$^{-2}$) was added on top of the vapour pressure of the solvents and immediately an equimolar mixture of carbon monoxide and ethylene (2×10$^5$ Nm$^{-2}$) added to the system through a pressure regulating valve set to 10×10$^5$ Nm$^{-2}$ above the solvent vapour pressure. Suitably, the molar ratio of ethylene to carbon monoxide in the reactor is approximately 9:1. The temperature of the reactor was maintained at 100° C. and as the reaction proceeded additional carbon monoxide and ethylene was added (on an equimolar basis) through the pressure regulating Tescom valve. No catalyst precipitation was observed.

Initial reaction rates measured in moles of methyl propanoate (MeP) per mole of palladium per hour and turnover measured in moles of methyl propanoate per mole of palladium were determined for the catalyst. This may be accomplished by an analysis of the amount of gas consumed per unit time (rate) and the total amount of gas consumed during the reaction, assuming ideal gas behaviour and 100% selectivity to methyl propanoate.

The reaction was repeated (Run 2) and initial reaction rates and turnover numbers calculated as described above.

The data for both runs is displayed in Table 1.

TABLE 1

|  | Maximum (moles MeP/mole Pd/hr) Initial Rate | Turnover (moles MeP/mole Pd/hr) number after 3 hours |
|---|---|---|
| Run 1 | 31,810 | 59,941 |
| Run 2 | 30,322 | 63,941 |

COMPARATIVE EXAMPLE 25

Preparation of Methyl Propanoate from Ethylene, Carbon Monoxide and Methanol Catalysed by a Known Catalyst Example 24 was repeated twice (Runs 3 and 4 respectively) except the catalyst system was as disclosed in WO 96/19434 and obtained by charging the autoclave with tri(dibenzylideneacetone)dipalladium ($1.44 \times 10^{-5}$ moles), 1,2 bis(di-t-butylphosphinomethyl)benzene ($7.61 \times 10^{-5}$ moles) and methane sulfonic acid ($2.25 \times 10^{-3}$ moles) in methyl propanoate/methanol (300 ml, 70 wt % methyl propanoate).

The initial reaction rates (moles MeP/mole Pd per hour) and turnover numbers (moles Pd/moles MeP) for the catalyst were calculated as described in Example 24 above. The results are presented in Table 2 below.

TABLE 2

|  | Maximum Initial Rate (moles Pd/moles MeP/hr) | Turnover number after 3 hours (moles Pd/mole MeP) |
|---|---|---|
| Run 3 | 29,730 | 48,386 |
| Run 4 | 30,335 | 51,997 |

The results demonstrate (see Table 1 and Table 2), that the catalyst of the present invention palladium 1,2-bis-(di-t-butylphosphinomethyl)ferrocene and the known palladium 1,2-bis(di-t-butylphosphinomethyl)benzene exhibit comparable initial catalytic reaction rates. However, the turnover number for the catalyst of the present invention is significantly higher than that for the known palladium 1,2-bis(di-t-butylphosphinomethyl)benzene catalyst, thereby indicating that the compound of the present invention increases the rate of the carbonylation reaction compared to the known bidentate system.

EXAMPLE 26

Preparation of Methyl Propanoate from Ethylene, Carbon Monoxide and Methanol Catalysed by a Compound of the Present Invention Example 24 was repeated (Runs 5 to 9 respectively) except the catalyst system employed was obtained by charging the autoclave with 1,2-bis-(di-1-adamantylphosphinomethyl)ferrocene-bis-methane sulphonate (Example 13 or 14, $7.61 \times 10^{-5}$ moles), tri(dibenzylideneacetone)dipalladium ($1.44 \times 10^{-5}$ moles) and methane sulfonic acid ($2.25 \times 10^{-3}$ moles) in methyl propanoate/methanol (300 ml, 70 wt % methyl propanoate)

The initial reaction rates (moles MeP/mole Pd per hour) and turnover numbers (moles Pd/moles MeP) for the catalyst were calculated as described in Example 24 above. The results are presented in Table 3 below.

TABLE 3

|  | Maximum Initial Rate (moles Pd/moles MeP/hr) | Turnover number after 3 hours (moles Pd/mole MeP) |
|---|---|---|
| Run 5 | 52,854 | 67,885 |
| Run 6 | 37,034 | 64,996 |
| Run 7 | 35,986 | 64,441 |
| Run 8 | 40,781 | 62,108 |
| Run 9 | 39,251 | 62,108 |

The results demonstrate (see Table 3 and Table 2), that the catalyst of the present invention palladium 1,2-bis(di-1-adamantylphosphinomethyl)ferrocene-bis-methane sulphonate exhibits a significantly higher initial catalytic rate and a significantly higher turnover number than the known catalyst palladium 1,2-bis-(di-t-butylphosphinomethyl)benzene, thereby indicating the compound of the present invention increases the rate of the carbonylation reaction compared to the known bidentate system.

The invention claimed is:

1. A compound obtainable by combining:
   (a) a Group VIIIB metal or a compound thereof; and,
   (b) a compound of formula I or salt thereof:

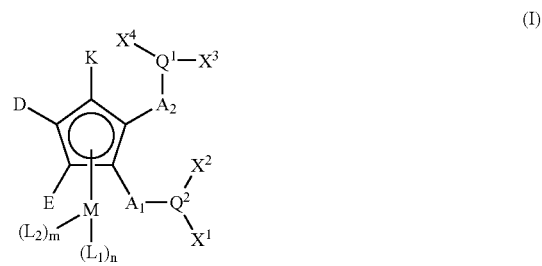

(I)

wherein:
$A_1$ and $A_2$, and $A_3$, $A_4$ and $A_5$ (when present), each independently represent lower alkylene;

K is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_3-Q^3(X^5)X^6$;

D is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $C(S)(R^{27})R^{28}$, $-SR^{29}$, $-C(O)SR^{30}$, $-CF_3$ or $A_4-Q^4(X^7)X^8$;

E is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_5-Q^5(X^9)X^{10}$;

or both D and E together with the carbon atoms of the cyclopentadienyl ring to which they are attached form an optionally substituted phenyl ring:

$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-adamantyl group, or $X^1$ and $X^2$ together with $Q^2$ to which they are attached form a ring system of formula Ia;

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-adamantyl group, or $X^3$ and $X^4$ together with $Q^1$ to which they are attached form a ring system of formula Ib;

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-adamantyl group, or $X^5$ and $X^6$ together with $Q^3$ to which they are attached form a ring system of formula Ic;

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-adamantyl group, or $X^7$ and $X^8$ together with $Q^4$ to which they are attached form a ring system of formula 1d;

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-adamantyl group, or $X^9$ and $X^{10}$ together with $Q^5$ to which they are attached form a ring system of formula Ie;

$Q^1$ and $Q^2$, and $Q^3$, $Q^4$ and $Q^5$ (when present), each independently represent phosphorus, arsenic or antimony;

M represents a Group VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

the ring systems of formula Ia, Ib, Ic, Id and Ie are represented by the formulae

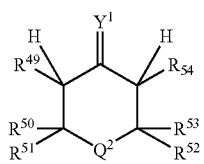
(Ia)

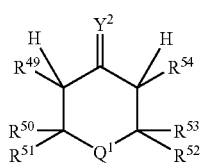
(Ib)

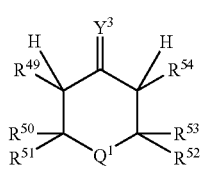
(Ic)

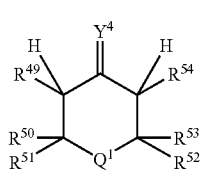
(Id)

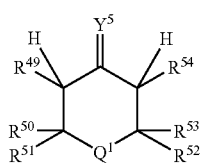
(Ie)

$R^{49}$, $R^{54}$ and $R^{55}$, each independently represent hydrogen, lower alkyl or aryl; $R^{50}$ to $R^{53}$ each independently represent hydrogen, lower alkyl, aryl or Het; and $Y^1$, $Y^2$, $Y^3$, $Y^4$ and $Y^5$, each independently represent oxygen, sulfur or N—$R^{55}$;

n=0 or 1;

and m=0 to 5;

provided that when n=1 then m equals 0, and when n equals 0 then m does not equal 0.

2. A compound as claimed in claim 1, wherein if both K represents -$A_3$-$Q^3(X^5)X^6$ and E represents -$A_5$-$Q^5(X^9)X^{10}$, then D represents -$A_4$-$Q^4(X^7)X^8$.

3. A compound as claimed in claim 1, wherein $R^1$ to $R^{18}$ and $R^{31}$ to $R^{42}$ each independently represent hydrogen, optionally substituted $C_1$-$C_6$ alkyl or optionally substituted phenyl.

4. A compound as claimed in claim 1, wherein $R^1$ to $R^{18}$ and $R^{31}$ to $R^{42}$ each independently represent hydrogen or non-substituted $C_1$-$C_6$ alkyl.

5. A compound as claimed in claim 1, wherein one or more of the groups $R^1$ to $R^3$, $R^4$ to $R^6$, $R^7$ to $R^9$, $R^{10}$ to $R^{12}$, $R^{13}$ to $R^{15}$, $R^{16}$ to $R^{18}$, $R^{31}$ to $R^{33}$, $R^{34}$ to $R^{36}$, $R^{37}$ to $R^{39}$, $R^{40}$ to $R^{42}$ together with the carbon atom to which they are attached each independently form a cyclic alkyl structure.

6. A compound as claimed in claim 1, wherein one or more of the groups $R^1$ and $R^2$, $R^4$ and $R^5$, $R^7$ and $R^8$, $R^{10}$ and $R^{11}$, $R^{13}$ and $R^{14}$, $R^{16}$ and $R^{17}$, $R^{31}$, and $R^{32}$, $R^{34}$ and $R^{35}$, $R^{37}$ and $R^{38}$, $R^{40}$ and $R^{41}$ together with the carbon atom to which they are attached each independently form a cyclic alkyl structure.

7. A compound as claimed in claim 1, wherein each of $R^1$ to $R^{18}$ and $R^{31}$ to $R^{42}$ does not represent hydrogen.

8. A compound as claimed in claim 1, wherein adamantyl represents unsubstituted adamantyl or adamantyl substituted with one or more unsubstituted $C_1$-$C_8$ alkyl substituents, or a combination thereof.

9. A compound as claimed in claim 1, wherein 2-phospha-adamantyl represents unsubstituted 2-phospha-adamantyl or 2-phospha-adamantyl substituted with one or more unsubstituted $C_1$-$C_8$ alkyl substituents, or a combination thereof.

10. A compound as claimed in claim 1, wherein 2-phospha-adamantyl includes one or more oxygen atoms in the 2-phospha-adamantyl skeleton.

11. A compound as claimed in claim 1, wherein congressyl represents unsubstituted congressyl.

12. A compound as claimed in claim 1, wherein $R^{50}$ to $R^{53}$ each independently represent optionally substituted $C_1$-$C_6$ alkyl, trifluoromethyl or phenyl optionally substituted with non-substituted $C_1$-$C_6$ alkyl or $OR^{19}$ where $R^{19}$ represents non-substituted $C_1$-$C_6$ alkyl.

13. A compound as claimed in claim 1, wherein $R^{49}$ and $R^{54}$ each independently represent hydrogen or non-substituted $C_1$-$C_6$ alkyl.

14. A compound as claimed in claim 1, wherein each of $Y^1$ to $Y^5$ represents oxygen.

15. A compound as claimed in claim 1, wherein $X^1$ is identical to $X^3$, and $X^5$, $X^7$ and $X^9$ when present.

16. A compound as claimed in claim 1, wherein $X^2$ is identical to $X^4$, and $X^6$, $X^8$ and $X^{10}$ when present.

17. A compound as claimed in claim 1, wherein $X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$.

18. A compound as claimed in claim 1, wherein $X^1$ represents $CR^1(R^2)(R^3)$, $X^2$ represents adamantyl, $X^3$ represents $CR^7(R^8)(R^9)$ and $X^4$ represents adamantyl.

19. A compound as claimed in claim 1, wherein $X^1$ represents $CR^1(R^2)(R^3)$, $X^2$ represents congressyl, $X^3$ represents $CR^7(R^8)(R^9)$ and $X^4$ represents congressyl.

20. A compound as claimed in claim 1, wherein $X^1$ to $X^4$ each independently represent adamantyl.

21. A compound as claimed in claim 1, wherein $X^1$ to $X^4$ each independently represent congressyl.

22. A compound as claimed in claim 1, wherein $X^1$ and $X^2$ together with $Q^2$ to which they are attached form a ring system of formula Ia, and $X^3$ and $X^4$ together with $Q^1$ to which they are attached form a ring system of formula Ib.

23. A compound as claimed in claim 1, wherein $X^1$ and $X^2$ together with $Q^2$ to which they are attached form a 2-phospha-adamantyl group, and $X^3$ and $X^4$ together with $Q^1$ to which they are attached form a 2-phospha-adamantyl group.

24. A compound as claimed in claim 1, wherein K represents hydrogen.

25. A compound as claimed in claim 1, wherein K represents $-A_3-Q^3(X^5)X^6$.

26. A compound as claimed in claim 25, wherein $-A_3-Q^3(X^5)X^6$ is identical to $-A_2-Q^1(X^3)X^4$.

27. A compound as claimed in claim 1, wherein D and E together with the carbon atoms of the cyclopentadienyl ring to which they are attached form an unsubstituted phenyl ring.

28. A compound as claimed in claim 1, wherein D and E both represent hydrogen.

29. A compound as claimed in claim 1, wherein D represents $-A_4-Q^4(X^7)X^8$.

30. A compound as claimed in claim 29, wherein $-A_4-Q^4(X^7)X^8$ is identical to $-A_2-Q^1(X^3)X^4$.

31. A compound as claimed in claim 29, wherein E represents hydrogen.

32. A compound as claimed in claim 1, wherein E represents $-A_5-Q^5(X^9)X^{10}$.

33. A compound as claimed in claim 32, wherein $-A_5-Q^5(X^9)X^{10}$ is identical to $-A_2-Q^1(X^3)X^4$.

34. A compound as claimed in claim 1, wherein $A_1$ and $A_2$, and $A_3$, $A_4$ and $A_5$ when present, each independently represent —$CH_2$— or —$C_2H_4$—.

35. A compound as claimed in claim 1, wherein each $A_1$ and $A_2$, and $A_3$, $A_4$ and $A_5$ when present are identical and preferably represent —$CH_2$—.

36. A compound as claimed in claim 1, wherein each $Q^1$ and $Q^2$, and $Q^3$, $Q^4$ and $Q^5$ when present are identical and preferably represent phosphorous.

37. A compound as claimed in claim 1, wherein n=1, m=0 and $L_1$ is selected from cyclopentadienyl, phenyl, indenyl or napthyl, preferably unsubstituted cyclopentadienyl.

38. A compound as claimed in claim 1, wherein M represents iron or a metal cation thereof.

39. A compound as claimed in claim 1 obtainable by combining: (a) palladium or a compound thereof; and (b) a compound of formula I as defined in claim 1.

40. A process for preparing a compound as defined in claim 1 comprising combining (a) a Group VIIIB metal or compound thereof; and, (b) a compound of formula I as defined in claim 1.

41. A compound of formula I

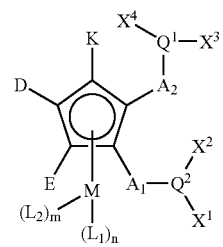

(I)

wherein $A_1$, $A_2$, K, D, E, M, $L_2$, $L_1$, $Q^1$, $Q^2$, $X^1$, $X^2$, $X^3$, $X^4$, n and m are as defined in claim 1.

42. A process for preparing a compound of formula I as defined in claim 41, comprising reacting a compound of formula II wherein $A_1$, $A_2$, K, D, E, M, $L_1$, $L_2$, n and m are as defined for a compound of formula I, and $LG_1$ and $LG_2$ represent suitable leaving groups, with a compound of formula IIIa and IIIb

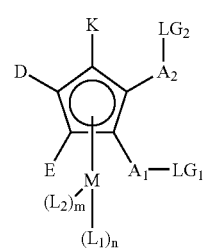

(II)

$HQ^2(X^1)X^2$ (IIIa)

$HQ^1(X^3)X^4$ (IIIb)

wherein $X^1$, $X^2$, $Q^2$, $X^3$, $X^4$ and $Q^1$ are as defined in claim 1.

43. A compound of formula II as defined in claim 42.

44. A process for preparing a compound of formula I wherein K, D, E, M, $A_2$, $A_1$, $L_2$, $L_1$, $Q^1$, $Q^2$, m and n are as defined in claim 1 and $X^1$ and $X^2$ together with $Q^2$ to which they are attached form a ring system of formula Ia as defined in claim 1 and $X^3$ and $X^4$ together with $Q^1$ to which they are attached form a ring system of formula Ib as defined in claim 1, comprising reacting a compound of formula XV

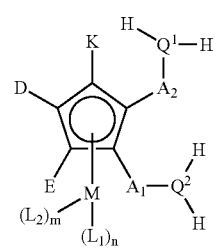

(XV)

wherein K, D, E, M, $A_2$, $A_1$, $L_2$, $L_1$, $Q^1$, $Q^2$, m and n are as defined in claim 1, with a compound of formula XVIa and XVIb

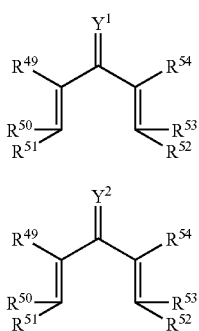
(XVIa)

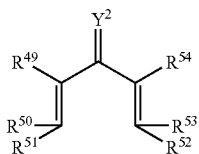
(XVIb)

wherein $Y^1$, $Y^2$, $R^{49}$ to $R^{55}$ are as defined for a compound of formula I.

45. A compound of formula XV as defined in claim 44.

46. A process for the carbonylation of an ethylenically unsaturated compound comprising contacting an ethylenically unsaturated compound with carbon monoxide and a co-reactant in the presence of a compound as defined in claim 1.

47. A process as defined in claim 46 wherein the co-reactant includes a hydroxyl group containing compound.

48. A process as claimed in claim 46, wherein the ethylenically unsaturated compound comprises ethylene, 1,3-butadiene, oct-1-ene or vinyl acetate, preferably ethylene.

49. A process as claimed in claim 46, further including the step of including a source of anions.

50. A composition comprising a compound as defined in claim 1 attached to a support.

51. A catalyst comprising a compound according to claim 1.

52. A catalyst comprising a composition according to claim 50.

* * * * *